US009296807B2

(12) United States Patent
Mineno et al.

(10) Patent No.: US 9,296,807 B2
(45) Date of Patent: *Mar. 29, 2016

(54) METHOD FOR EXPRESSION OF SPECIFIC GENE

(71) Applicants: TAKARA BIO INC., Otsu-shi, Shiga (JP); MIE UNIVERSITY, Tsu-shi, Mie (JP)

(72) Inventors: Junichi Mineno, Otsu (JP); Sachiko Okamoto, Otsu (JP); Risa Sumioka, Otsu (JP); Masanari Kitagawa, Otsu (JP); Hiroshi Shiku, Tsu (JP); Ikunoshin Kato, Otsu (JP)

(73) Assignees: TAKARA BIO INC., Shiga (JP); MIE UNIVERSITY, Mie (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/701,929

(22) Filed: May 1, 2015

(65) Prior Publication Data

US 2015/0232530 A1  Aug. 20, 2015

Related U.S. Application Data

(62) Division of application No. 12/664,133, filed as application No. PCT/JP2008/060618 on Jun. 10, 2008, now Pat. No. 9,051,391.

(30) Foreign Application Priority Data

Jun. 11, 2007 (JP) .................................. 2007-154351

(51) Int. Cl.
*C12P 21/06* (2006.01)
*C12N 5/00* (2006.01)
*C12N 15/63* (2006.01)
*C07K 14/725* (2006.01)
*C12N 15/85* (2006.01)

(52) U.S. Cl.
CPC ............ *C07K 14/7051* (2013.01); *C12N 15/85* (2013.01); *C12N 2800/40* (2013.01); *C12N 2840/102* (2013.01)

(58) Field of Classification Search
None
See application file for complete search history.

(56) References Cited

U.S. PATENT DOCUMENTS 9,051,391 B2 *   6/2015   Mineno et al.

FOREIGN PATENT DOCUMENTS

JP   2004526422 A   9/2004
WO   0244321 A2    6/2002

OTHER PUBLICATIONS

Office Action dated Sep. 2, 2014, in corresponding Japanese Patent Application No. 2013-101543,
Pogulis et al.,"A Retroviral Vector That Directs Simultaneous Expression of α and β T Cell Receptor Genes," Human Gene Therapy, 1998, pp. 2299-2304, vol. 9, Mary Ann Liebert, Inc.
Van Der Veken et al.,"αβT-Cell Receptor Engineered γδ T Cells Mediate Effective Antileukemic Reactivity," Cancer Research, 2006, pp. 3331-3337, vol. 66.
Pinthus et al.,"Adoptive Immunotherapy of Prostate Cancer Bone Lesions Using Redirected Effector Lymphocytes," The Journal of Clinical Investigation, 2004, pp. 1774-1781, vol. 114, No. 12.
Fujio et al.,"Funotional Reconstitution of Class II MHC-Restricted T Cell Immunity Mediated by Retroviral Transfer of the {alpha}{beta} TCR COMPLEX," The Journal of Immunology, 2000, pp. 528-532, vol. 165, The American Association of Immunologists, Inc., Bethesda, MD, USA.
Clay et al.,"Efficient Transfer of a Tumor Antigen-Reaciive TCR to Human Peripheral Blood Lymphocytes Confers Anti-Tumor Reactivity," The Journal of Immunology, 1999, pp. 507-513, vol. 163, The American Association of Immunologists, Inc., Bethesda, MD, USA.
Schaft et al.,"Peptide Fine Specificity of Anti-Glycoprotein 100 CTL Is Preserved Following Transfer of Engineered TCR {alpha}{beta} Genes Into Primary Human T Lymphocytes," The Journal of Immunology, 2003, pp. 2186-2194, vol. 170, The American Association of Immunologists, Inc., Bethesda, MD, USA.
Heemskerk et al.,"Redirection of Antileukemic Reactivity of Peripheral T Lymphocytes Using Gene Transfer of Minor Histocompatibility Antigen Ha-2-Specific T-Cell Receptor Complexes Expressing a Conserved Alpha Joining Region," The American Society of Hematology, 2003, pp. 3530-3540, vol. 102, No. 10.
Willemsen et al.,"Grafting Primary Human T Lymphocytes With Cancer-Specific Chimeric Single Chain and Two Chain TCR" Gene Therapy, 2000, pp. 1369-1377, vol. 7.
International Preliminary Report on Patentability, PCT/JP2008/060618, issued Jun. 10, 2008.
Search Report issued by the Chinese Patent Office in Chinese patent application 200880102998.9 on Oct. 26, 2011.
Extended European search report dated Dec. 7, 2010, issued in corresponding application EP 08777135.8.
Samakogku et al, "A genetic strategy to treat sickle cell anemia by coregulating globin transgene expression and D RNA interference," Nature Biotechnology, 24(1 ): 89-94 (Jan. 1, 2006).
Greber et al, "Multi-gene engineering: Simultaneous expression and knockdown of six genes of a single platform" Biotechnology and Bioengineering, 96(5): 821-834 (Apr. 1, 2007).

(Continued)

*Primary Examiner* — Doug Schultz
(74) *Attorney, Agent, or Firm* — Browdy and Neimark, PLLC

(57) ABSTRACT

Disclosed is a cell which can express a non-natural oligomeric protein, which has, introduced therein, a gene encoding an exogenous polypeptide corresponding to at least one endogenous polypeptide constituting a natural oligomeric protein, and in which the expression of the endogenous polypeptide is inhibited.

2 Claims, 15 Drawing Sheets

(56) References Cited

OTHER PUBLICATIONS

Cohen et al, "Enhanced antitumor activity of murine-human hybrid T-cell receptor (TCR) in human lymphocytes is associated with improved pairing and TCR/CD3 stability" Cancer Res 66(17): 8878-8886 (Sep. 1, 2006).

Kuball et al, "Facilitating matched pairing and expression of TCR chains introduced into human T cells" Blood, American Society of Hematology, 109(6): 2331-2338 (Mar. 15, 2007).

Sommermeyer et al "Designer T cells by T cell receptor replacement" European Journal of Immunology 36(11): 3052-3059 (Nov. 1, 2006).

Second Office Action issued Aug. 10, 2012, in corresponding Chinese Patent Application No. 200880102998.9, and English translation thereof.

Office Action issued Jan. 15, 2013, in corresponding Japanese Patent Application No. 2009-519261, and English translation thereof.

Office Action issued Apr. 13, 2013, in corresponding Korean Patent Application No. 10-2010-7000445, and English translation thereof.

Scholten et al., Codon modification of T cell receptors allows enhanced functional expression in transgenic human T cells, Clinical Immunology, 119(2):135-145 (2006).

Office Action issued May 6, 2013, in corresponding European Patent Application No. 08777135.8.

Semizarov et al., Specificity of short interfering RNA determined through gene expressing signatures, PNAS, 100 (11):6347-6352 (2003).

Kiang et al. Mol. Ther. vol. 12, No. 3, Sep. 2005, pp. 555-561.

\* cited by examiner

SEQUENCE LISTING

```
<160> NUMBER OF SEQ ID NOS: 35

<210> SEQ ID NO 1
<211> LENGTH: 918
<212> TYPE: DNA
<213> ORGANISM: Artificial sequence
<220> FEATURE:
<223> OTHER INFORMATION: Codon modified anti-MAGE A4 TCR alpha chain.
<220> FEATURE:
<221> NAME/KEY: misc_feature
<223> OTHER INFORMATION: synthetic
```

<400> SEQUENCE: 1

```
ggtaccgaat tcaaggaaaa aagcggccgc taatacgact cactataggg cctgcaggag      60
ctccgccatg ctgctgctgc tgatccccgt gctgggcatg atcttcgccc tgcgggacgc     120
cagagcccag agcgtgagcc agcacaacca ccacgtgatc ctgagcgagg ccgccagcct     180
ggaactgggc tgcaactaca gctacggcgg caccgtgaac ctgttttggt acgtgcagta     240
ccccggccag cacctgcagc tgctgctgaa gtactttagc ggcgaccccc tggtgaaggg     300
catcaagggc ttcgaggccg agttcatcaa gagcaagttc agcttcaacc tgcggaagcc     360
cagccgtcag tggagcgaca ccgccgagta cttttgcgcc ggcagaggcg gcggaaacaa     420
gctgaccttc ggcaccggca cccagctgaa ggtggagctg aacatccaga accccgaccc     480
cgccgtgtac cagctgcggg acagcaagag cagcgacaag agcgtgtgcc tgttcaccga     540
cttcgacagc cagaccaacg tgagccagag caaggacagc acgtgtaca tcaccgacaa     600
gaccgtgctg gacatgcgga gcatggactt caagagcaac agcgccgtgg cctggtccaa     660
caagagcgac ttcgcctgcg ccaacgcctt caacaacagc atcatccccg aggacacctt     720
tttccccagc cccgagagca gctgcgacgt gaaactggtg gagaagagct tcgagaccga     780
caccaacctg aacttccaga atctgagcgt gatcggcttc cggatcctgc tgctgaaagt     840
ggccggcttc aatctgctga tgaccctgcg gctgtggagc agctgacctg cagggcggcc     900
gcaaaaggaa aactcgag                                                   918
```

<210> SEQ ID NO 2
<211> LENGTH: 1041
<212> TYPE: DNA
<213> ORGANISM: Artificial sequence
<220> FEATURE:
<223> OTHER INFORMATION: Codon modified anti-MAGE A4 TCR beta chain.
<220> FEATURE:
<221> NAME/KEY: misc_feature
<223> OTHER INFORMATION: synthetic

<400> SEQUENCE: 2

```
ggtaccgaat tcaaggaaaa aagcggccgc taatacgact cactataggg cctgcaggga      60
ccccgccatg ggcaccagcc tgctgtgctg gatggccctg tgcctgctgg cgccgacca     120
cgccgatacc ggcgtgagcc agaacccccg cacaagatc accaagcggg gccagaacgt     180
gaccttcaga tgcgacccca tcagcgagca aaccggctg tactggtaca ggcagacact     240
gggccagggc cccgagttcc tgaccctact tccagaacgag gcccagctgg aaaagagccg     300
gctgctgtcc gaccggttca gcgccgagcg gcccaagggc agcttcagca ccctggaaat     360
ccagcggacc gagcagggcg acagcgccat gtacctgtgc gccagcagcc tggctcaggg     420
agccggcgag acccagtact cggccctgg caccggctg ctggtgctgg aagatctgaa     480
gaacgtgttc ccccccgagg tggcgtgtt cgagcccagc gaggccgaga tcagccacac     540
ccagaaagcc accctggtgt gcctggccac cggcttctac cccgaccacg tggagctgtc     600
ttggtgggtg aacggcaaag aggtgcacag cggcgtcagc accgacccc agcccctgaa     660
agagcagccc gccctgaacg acagccgta ctgcctgagc agcggctga gagtgagcgc     720
caccttctgg cagaacccca ggaaccactt ccgctgtcag gtgcagttct acggcctgag     780
cgagaacgac gagtggaccc aggacagagc caagccgtg acccagatcg tgagcgccga     840
ggcctggggc agagccgact gcggcttcac cagcgagagc taccagcagg gcgtgctgtc     900
cgccaccatc ctgtacgaga tcctgctggg caaggccacc ctgtacgccg tgctggtgtc     960
```

-continued

```
cgccctggtg ctgatggcca tggtgaagcg gaaggacagc cggggctgac ctgcagggcg    1020
gccgcaaaag gaaaactcga g                                              1041

<210> SEQ ID NO 3
<211> LENGTH: 21
<212> TYPE: DNA
<213> ORGANISM: Artificial sequence
<220> FEATURE:
<223> OTHER INFORMATION: Synthetic chimera oligonucleotide for siRNA-A.
      Nucleotides 1 to 19 are ribonucleotides-other nucleotides are
      deoxyribonucleotides
<220> FEATURE:
<221> NAME/KEY: misc_feature
<223> OTHER INFORMATION: synthetic

<400> SEQUENCE: 3
guaaggauuc ugauguguat t                                              21

<210> SEQ ID NO 4
<211> LENGTH: 21
<212> TYPE: DNA
<213> ORGANISM: Artificial sequence
<220> FEATURE:
<223> OTHER INFORMATION: Synthetic chimera oligonucleotide for siRNA-A.
      Nucleotides 1 to 19 are ribonucleotides-other nucleotides are
      deoxyribonucleotides
<220> FEATURE:
<221> NAME/KEY: misc_feature
<223> OTHER INFORMATION: synthetic

<400> SEQUENCE: 4
uacacaucag aauccuuact t                                              21

<210> SEQ ID NO 5
<211> LENGTH: 21
<212> TYPE: DNA
<213> ORGANISM: Artificial sequence
<220> FEATURE:
<223> OTHER INFORMATION: Synthetic chimera oligonucleotide for siRNA-B.
      Nucleotides 1 to 19 are ribonucleotides-other nucleotides are
      deoxyribonucleotides
<220> FEATURE:
<221> NAME/KEY: misc_feature
<223> OTHER INFORMATION: synthetic

<400> SEQUENCE: 5
ccaccauccu cuaugagaut t                                              21

<210> SEQ ID NO 6
<211> LENGTH: 21
<212> TYPE: DNA
<213> ORGANISM: Artificial sequence
<220> FEATURE:
<223> OTHER INFORMATION: Synthetic chimera oligonucleotide for siRNA-B.
      Nucleotides 1 to 19 are ribonucleotides-other nucleotides are
      deoxyribonucleotides
<220> FEATURE:
<221> NAME/KEY: misc_feature
<223> OTHER INFORMATION: synthetic

<400> SEQUENCE: 6
aucucauaga ggaugguggt t                                              21

<210> SEQ ID NO 7
<211> LENGTH: 21
<212> TYPE: DNA
<213> ORGANISM: Artificial sequence
<220> FEATURE:
```

```
<223> OTHER INFORMATION: Synthetic chimera oligonucleotide for siRNA-C.
      Nucleotides 1 to 19 are ribonucleotides-other nucleotides are
      deoxyribonucleotides
<220> FEATURE:
<221> NAME/KEY: misc_feature
<223> OTHER INFORMATION: synthetic

<400> SEQUENCE: 7
ccaauuacgc guugguagct t                                                    21

<210> SEQ ID NO 8
<211> LENGTH: 21
<212> TYPE: DNA
<213> ORGANISM: Artificial sequence
<220> FEATURE:
<223> OTHER INFORMATION: Synthetic chimera oligonucleotide for siRNA-C.
      Nucleotides 1 to 19 are ribonucleotides-other nucleotides are
      deoxyribonucleotides
<220> FEATURE:
<221> NAME/KEY: misc_feature
<223> OTHER INFORMATION: synthetic

<400> SEQUENCE: 8
gcuaccaacg cguaauuggt t                                                    21

<210> SEQ ID NO 9
<211> LENGTH: 21
<212> TYPE: DNA
<213> ORGANISM: Artificial sequence
<220> FEATURE:
<223> OTHER INFORMATION: Synthetic oligonucleotide primer for wild-type
      TCR alpha chain.
<220> FEATURE:
<221> NAME/KEY: misc_feature
<223> OTHER INFORMATION: synthetic

<400> SEQUENCE: 9
gtgcaaacgc cttcaacaac a                                                    21

<210> SEQ ID NO 10
<211> LENGTH: 23
<212> TYPE: DNA
<213> ORGANISM: Artificial sequence
<220> FEATURE:
<223> OTHER INFORMATION: Synthetic oligonucleotide primer for wild-type
      TCR alpha chain.
<220> FEATURE:
<221> NAME/KEY: misc_feature
<223> OTHER INFORMATION: synthetic

<400> SEQUENCE: 10
gaccagcttg acatcacagg aac                                                  23

<210> SEQ ID NO 11
<211> LENGTH: 21
<212> TYPE: DNA
<213> ORGANISM: Artificial sequence
<220> FEATURE:
<223> OTHER INFORMATION: Synthetic oligonucleotide primer for
      codon-modified TCR alpha chain.
<220> FEATURE:
<221> NAME/KEY: misc_feature
<223> OTHER INFORMATION: synthetic

<400> SEQUENCE: 11
agagcttcga gaccgacacc a                                                    21

<210> SEQ ID NO 12
<211> LENGTH: 19
```

```
<212> TYPE: DNA
<213> ORGANISM: Artificial sequence
<220> FEATURE:
<223> OTHER INFORMATION: Synthetic oligonucleotide primer for
      codon-modified TCR alpha chain.
<220> FEATURE:
<221> NAME/KEY: misc_feature
<223> OTHER INFORMATION: synthetic

<400> SEQUENCE: 12
tgaagccggc cactttcag                                                    19

<210> SEQ ID NO 13
<211> LENGTH: 22
<212> TYPE: DNA
<213> ORGANISM: Artificial sequence
<220> FEATURE:
<223> OTHER INFORMATION: Synthetic oligonucleotide primer for wild-type
      TCR beta chain.
<220> FEATURE:
<221> NAME/KEY: misc_feature
<223> OTHER INFORMATION: synthetic

<400> SEQUENCE: 13
cgccctcaat gactccagat ac                                                22

<210> SEQ ID NO 14
<211> LENGTH: 20
<212> TYPE: DNA
<213> ORGANISM: Artificial sequence
<220> FEATURE:
<223> OTHER INFORMATION: Synthetic oligonucleotide primer for wild-type
      TCR beta chain.
<220> FEATURE:
<221> NAME/KEY: misc_feature
<223> OTHER INFORMATION: synthetic

<400> SEQUENCE: 14
cctgggtcca ctcgtcattc                                                   20

<210> SEQ ID NO 15
<211> LENGTH: 20
<212> TYPE: DNA
<213> ORGANISM: Artificial sequence
<220> FEATURE:
<223> OTHER INFORMATION: Synthetic oligonucleotide primer for
      codon-modified TCR beta chain.
<220> FEATURE:
<221> NAME/KEY: misc_feature
<223> OTHER INFORMATION: synthetic

<400> SEQUENCE: 15
ggcttcacca gcgagagcta                                                   20

<210> SEQ ID NO 16
<211> LENGTH: 18
<212> TYPE: DNA
<213> ORGANISM: Artificial sequence
<220> FEATURE:
<223> OTHER INFORMATION: Synthetic oligonucleotide primer for
      codon-modified TCR beta chain.
<220> FEATURE:
<221> NAME/KEY: misc_feature
<223> OTHER INFORMATION: synthetic

<400> SEQUENCE: 16
tcaccatggc catcagca                                                     18

<210> SEQ ID NO 17
```

```
<211> LENGTH: 19
<212> TYPE: DNA
<213> ORGANISM: Artificial sequence
<220> FEATURE:
<223> OTHER INFORMATION: Synthetic oligonucleotide primer for
      beta-actin.
<220> FEATURE:
<221> NAME/KEY: misc_feature
<223> OTHER INFORMATION: synthetic

<400> SEQUENCE: 17
attgccgaca ggatgcaga                                                  19

<210> SEQ ID NO 18
<211> LENGTH: 21
<212> TYPE: DNA
<213> ORGANISM: Artificial sequence
<220> FEATURE:
<223> OTHER INFORMATION: Synthetic oligonucleotide primer for
      beta-actin.
<220> FEATURE:
<221> NAME/KEY: misc_feature
<223> OTHER INFORMATION: synthetic

<400> SEQUENCE: 18
gagtacttgc gctcaggagg a                                               21

<210> SEQ ID NO 19
<211> LENGTH: 21
<212> TYPE: DNA
<213> ORGANISM: Artificial sequence
<220> FEATURE:
<223> OTHER INFORMATION: Portion of TCR alpha chain.
<220> FEATURE:
<221> NAME/KEY: misc_feature
<223> OTHER INFORMATION: synthetic

<400> SEQUENCE: 19
agtaaggatt ctgatgtgta t                                               21

<210> SEQ ID NO 20
<211> LENGTH: 21
<212> TYPE: DNA
<213> ORGANISM: Artificial sequence
<220> FEATURE:
<223> OTHER INFORMATION: Portion of codon-modified TCR alpha chain.
<220> FEATURE:
<221> NAME/KEY: misc_feature
<223> OTHER INFORMATION: synthetic

<400> SEQUENCE: 20
agcaaggaca gcgacgtgta c                                               21

<210> SEQ ID NO 21
<211> LENGTH: 7
<212> TYPE: PRT
<213> ORGANISM: Artificial sequence
<220> FEATURE:
<223> OTHER INFORMATION: Portion of TCR alpha chain.
<220> FEATURE:
<221> NAME/KEY: misc_feature
<223> OTHER INFORMATION: synthetic

<400> SEQUENCE: 21

Ser Lys Asp Ser Asp Val Tyr
1               5

<210> SEQ ID NO 22
<211> LENGTH: 21
```

```
<212> TYPE: DNA
<213> ORGANISM: Artificial sequence
<220> FEATURE:
<223> OTHER INFORMATION: Portion of TCR beta chain.
<220> FEATURE:
<221> NAME/KEY: misc_feature
<223> OTHER INFORMATION: synthetic

<400> SEQUENCE: 22
gccaccatcc tctatgagat c                                              21

<210> SEQ ID NO 23
<211> LENGTH: 21
<212> TYPE: DNA
<213> ORGANISM: Artificial sequence
<220> FEATURE:
<223> OTHER INFORMATION: Portion of codon-modified TCR beta chain.
<220> FEATURE:
<221> NAME/KEY: misc_feature
<223> OTHER INFORMATION: synthetic

<400> SEQUENCE: 23
gccaccatcc tgtacgagat c                                              21

<210> SEQ ID NO 24
<211> LENGTH: 7
<212> TYPE: PRT
<213> ORGANISM: Artificial sequence
<220> FEATURE:
<223> OTHER INFORMATION: Portion of TCR beta chain.
<220> FEATURE:
<221> NAME/KEY: misc_feature
<223> OTHER INFORMATION: synthetic

<400> SEQUENCE: 24

Ala Thr Ile Leu Tyr Glu Ile
1               5

<210> SEQ ID NO 25
<211> LENGTH: 39
<212> TYPE: DNA
<213> ORGANISM: Artificial sequence
<220> FEATURE:
<223> OTHER INFORMATION: Synthetic oligonucleotide primer pPGK5.
<220> FEATURE:
<221> NAME/KEY: misc_feature
<223> OTHER INFORMATION: synthetic

<400> SEQUENCE: 25
acgcgtgcgg ccgcagatct aattctaccg ggtagggga                           39

<210> SEQ ID NO 26
<211> LENGTH: 39
<212> TYPE: DNA
<213> ORGANISM: Artificial sequence
<220> FEATURE:
<223> OTHER INFORMATION: Synthetic oligonucleotide primer pPGK3.
<220> FEATURE:
<221> NAME/KEY: misc_feature
<223> OTHER INFORMATION: synthetic

<400> SEQUENCE: 26
ctcgaggcgg cgcggatccc tgcaggtcga aggcccgg                            39

<210> SEQ ID NO 27
<211> LENGTH: 34
<212> TYPE: DNA
<213> ORGANISM: Artificial sequence
<220> FEATURE:
```

```
<223> OTHER INFORMATION: Synthetic oligonucleotide primer 3MSCV5.
<220> FEATURE:
<221> NAME/KEY: misc_feature
<223> OTHER INFORMATION: synthetic

<400> SEQUENCE: 27
tacctcgagc gataaaataa aagattttat ttag                                34

<210> SEQ ID NO 28
<211> LENGTH: 45
<212> TYPE: DNA
<213> ORGANISM: Artificial sequence
<220> FEATURE:
<223> OTHER INFORMATION: Synthetic oligonucleotide primer 3MSCV3.
<220> FEATURE:
<221> NAME/KEY: misc_feature
<223> OTHER INFORMATION: synthetic

<400> SEQUENCE: 28
tacgaattcg attgaatccg tcgactgaaa gacccccgct gacgg                    45

<210> SEQ ID NO 29
<211> LENGTH: 69
<212> TYPE: DNA
<213> ORGANISM: Artificial sequence
<220> FEATURE:
<223> OTHER INFORMATION: Synthetic oligonucleotide for pSINsi-hU6-TCRA.
<220> FEATURE:
<221> NAME/KEY: misc_feature
<223> OTHER INFORMATION: synthetic

<400> SEQUENCE: 29
gatccgtaag gattctgatg tgtacacagg gaagcgagtc tgtacacatc agaatcctta    60
cttttttat                                                            69

<210> SEQ ID NO 30
<211> LENGTH: 67
<212> TYPE: DNA
<213> ORGANISM: Artificial sequence
<220> FEATURE:
<223> OTHER INFORMATION: Synthetic oligonucleotide for pSINsi-hU6-TCRA.
<220> FEATURE:
<221> NAME/KEY: misc_feature
<223> OTHER INFORMATION: synthetic

<400> SEQUENCE: 30
cgataaaaaa gtaaggattc tgatgtgtac agactcgctt ccctgtgtac acatcagaat    60
ccttacg                                                              67

<210> SEQ ID NO 31
<211> LENGTH: 67
<212> TYPE: DNA
<213> ORGANISM: Artificial sequence
<220> FEATURE:
<223> OTHER INFORMATION: Synthetic oligonucleotide for pBAsi-mU6-TCRB.
<220> FEATURE:
<221> NAME/KEY: misc_feature
<223> OTHER INFORMATION: synthetic

<400> SEQUENCE: 31
gatccgccac catcctctat gagattagtg ctcctggttg atctcataga ggatggtggc    60
tttttta                                                              67

<210> SEQ ID NO 32
<211> LENGTH: 67
<212> TYPE: DNA
```

<213> ORGANISM: Artificial sequence
<220> FEATURE:
<223> OTHER INFORMATION: Synthetic oligonucleotide for pBAsi-mU6-TCRB.
<220> FEATURE:
<221> NAME/KEY: misc_feature
<223> OTHER INFORMATION: synthetic

<400> SEQUENCE: 32
agcttaaaaa agccaccatc ctctatgaga tcaaccagga gcactaatct catagaggat    60
ggtggcg                                                              67

<210> SEQ ID NO 33
<211> LENGTH: 357
<212> TYPE: DNA
<213> ORGANISM: Artificial sequence
<220> FEATURE:
<223> OTHER INFORMATION: Synthetic oligonucleotide for
      TCR-loop-MluI/SacII.
<220> FEATURE:
<221> NAME/KEY: misc_feature
<223> OTHER INFORMATION: synthetic

<400> SEQUENCE: 33
cccggatccg taagtacgcg ttatttcaaa tttagcagga aaaagagaa catcaccttg     60 taaaactgaa gattgtgacc agtcagaata atgtgtaagg attctgatgt gtacacaggg   120
aagcgagtct gtacacatca gaatccttac agcattatgg tgacagctgc ctcgggaagc   180
caagttgggc tttaaagtgc agggcctgct gatgttgagt gcttttgtt cccaccatcc    240 tctatgagat tagtgctcct ggttgatctc atagaggatg gtggggcata agaagttatg   300
tattcatcca ataattcaag ccaagcaagt ataggtgt tttaatagcc gcgggg         357

<210> SEQ ID NO 34
<211> LENGTH: 20
<212> TYPE: DNA
<213> ORGANISM: Artificial sequence
<220> FEATURE:
<223> OTHER INFORMATION: Oligonucleotide primer for amplification of
      GAPDH gene.
<220> FEATURE:
<221> NAME/KEY: misc_feature
<223> OTHER INFORMATION: synthetic

<400> SEQUENCE: 34
atggtggtga agacgccagt                                                20

<210> SEQ ID NO 35
<211> LENGTH: 20
<212> TYPE: DNA
<213> ORGANISM: Artificial sequence
<220> FEATURE:
<223> OTHER INFORMATION: Oligonucleotide primer for amplification of
      GAPDH gene.
<220> FEATURE:
<221> NAME/KEY: misc_feature
<223> OTHER INFORMATION: synthetic

<400> SEQUENCE: 35
gcaccgtcaa ggctgagaac                                                20

METHOD FOR EXPRESSION OF SPECIFIC GENE

TECHNICAL FIELD

The present invention relates to a cell expressing a non-natural oligomeric protein, a process for producing the cell, and a method for forming a non-natural oligomeric protein, which are useful in the medical field.

BACKGROUND ART

A living body is protected from exogenous matters mainly by immunological responses, and immune systems are constructed by various cells and soluble factors made by the cells. Among them, leukocytes, particularly lymphocytes play a central role. The lymphocytes are classified into two main types called B lymphocytes (hereinafter, referred to as B cells in some cases) and T lymphocytes (hereinafter, referred to as T cells in some cases), and either of them specifically recognizes an antigen, and acts on it to defend a living body.

Most of the T cells are composed of CD4 positive T cells expressing a CD (Cluster of Differentiation) 4 marker and CD8 positive T cells expressing a CD8 marker, at the periphery. Most of the CD4 positive T cells are called helper T cells (hereinafter, referred to as $T_H$), and are involved in assistance of antibody production and inducement of various immunological responses, and are differentiated into a Th1 type and a Th2 type in which the kinds of cytokines produced by antigen stimulation are different from each other. Most of the CD8 positive T cells are differentiated into cytotoxic T cells [Tc: cytotoxic T lymphocytes, also called as killer T cells, hereinafter, referred to as a CTL in some cases] exhibiting cytotoxic activity by antigen stimulation.

As a fourth cancer therapy next to surgical operation, chemotherapy, and radiation therapy, immunotherapy has been drawing attention recently. Since the immunotherapy utilizes the immunological ability originally possessed by human beings, it is said that the physical burden on a patient is smaller as compared with other therapies. The known immunotherapy include a therapy for introducing lymphokine activating cells, NKT cells, a γδT cells, etc. obtained from in vitro induced CTL, peripheral blood lymphocytes by expansion-culturing according to a variety of methods, a dendritic cell transferring therapy and a peptide vaccine therapy expecting in vivo inducement of antigen-specific CTL, a Th1 cell therapy and, further, an immune gene therapy in which a gene from which various effects can be expected is introduced into these cells in vitro, followed by transferring into a body.

Some of cytotoxic T cells (CTL) recognize a complex which is a binding material of a major histocompatibility antigen molecule (MHC molecule, in the case of human beings, called a human leukocyte antigen, hereinafter, abbreviated as an HLA) encoded by a major histocompatibility gene complex (hereinafter, abbreviated as an MHC) and an antigenic peptide, with a specific T cell receptor (hereinafter, abbreviated as a TCR) composed of a heterodimer of an α chain and a β chain, and can damage a cell presenting the complex on its surface.

It is expected to impart cytotoxic activity specific to an objective antigen to a T cell having cytotoxic activity including a CTL by introducing a TCR gene recognizing the objective antigen into the T cell. Based on this expectation, a gene therapy with a TCR gene targeting various antigens such as MART1 (Non-Patent Document 1), gp100 (Non-Patent Document 2) and an mHAG HA-2 antigen (Non-Patent Document 3) have been tried. However, for example, when a TCR gene composed of an α chain and a β chain recognizing an objective antigen is introduced into a T cell, the endogenous TCR α chain and TCR β chain originally expressed by the T cell cause mispairing between a β chain and an α chain of the introduced TCR recognizing the objective antigen. That is, when α' and β' are introduced into a cell expressing α and β, each heterodimer of αβ, αβ', α'β, and α'β' is formed, thereby causing a problem that TCRs forming a proper heterodimer to recognize the objective antigen are decreased, and a heterodimer recognizing an unexpected antigen may be formed.

As a method for solving this problem, a method of introducing a single-stranded TCR which does not form a heterodimer with an endogenous TCR into a T cell (Non-Patent Document 4), and a method of introducing a chimeric receptor (T-body) with an antibody recognizing an objective antigen into a T cell (Non-Patent Document 5) have been tried. However, since a T cell obtained by these methods have both of an endogenous TCR and an introduced TCR, the T cell may recognize two kinds of antigens. Further, since a recombinant TCR is not a naturally occurring TCR, it is necessary to confirm signal transmission to a T cell, safety, etc. In addition, as another method, there is a method of introducing a β chain and an α chain of a TCR recognizing an objective antigen into a T cell not expressing an α chain and a β chain of a TCR, for example, a T cell (γδ cell) expressing a γ chain and a δ chain (Non-Patent Document 6). However, a T cell obtained by this method has the same concern as that of the method of using a recombinant TCR.

As illustrated above by the TCR, when a exogenous polypeptide which can be incorporated into an oligomeric protein as a constituent polypeptide is introduced into a cell expressing the protein, there are problems that an oligomeric protein which is not capable of manifesting the desired function and in which an endogenous polypeptide and a exogenous polypeptide are mixed may be formed, or an oligomeric protein manifesting the desired function may be decreased by the competition between an endogenous polypeptide and a exogenous polypeptide.

Non-Patent Document 1: J. Immunol., vol. 163, pp. 507-513 (1999)

Non-Patent Document 2: J. Immunol., vol. 170, pp. 2186-2194 (2003)

Non-Patent Document 3: Blood, vol. 103, pp. 3530-3540 (2003)

Non-Patent Document 4: Gene Therapy, vol. 7, pp. 1369-1377 (2000)

Non-Patent Document 5: J. Clin. Invest., vol. 114, pp. 1774-1781 (2004)

Non-Patent Document 6: Cancer Res., vol. 66, pp. 3331-3337 (2006)

DISCLOSURE OF THE INVENTION

Problems to be Solved by the Invention

An object of the present invention is to provide a cell in which undesired oligomer formation by mixing endogenous and exogenous polypeptides caused upon introduction of a gene encoding a exogenous polypeptide capable of constituting an oligomeric protein into a cell expressing the oligomeric protein is inhibited, and a method of inhibiting the oligomer formation.

Means for Solving the Problems

The first aspect of the present invention relates to a cell expressing a non-natural oligomeric protein, which comprises an introduced gene which encodes an exogenous polypeptide constituting the non-natural oligomeric protein corresponding to at least one endogenous polypeptide constituting a natural oligomeric protein, wherein the expression of the endogenous polypeptide is inhibited.

In the first aspect of the present invention, the oligomeric protein may be composed of a variable region and a constant region, and the oligomeric protein may be an antigen recognition receptor, in particular, the antigen recognition receptor may be a T cell receptor (TCR). Further, the expression of the endogenous polypeptide may be inhibited by RNA interference, and the oligomeric protein may be composed of a variable region and a constant region, and the expression of the endogenous polypeptide constituting the oligomeric protein may be inhibited by RNA interference targeting a sequence of an mRNA corresponding to the constant region of the polypeptide. Furthermore, the exogenous polypeptide may have a constant region of the same amino acid sequence as that of the endogenous polypeptide, and the expression of the endogenous polypeptide may be inhibited by making a nucleotide sequence of an mRNA of the exogenous polypeptide differ from a nucleotide sequence of an mRNA of the endogenous polypeptide.

The second aspect of the present invention relates to a process for producing a cell expressing a non-natural oligomeric protein, which comprises carrying out the following steps:

(a) a step of introducing a gene encoding an exogenous polypeptide constituting the non-natural oligomeric protein corresponding to at least one endogenous polypeptide constituting a natural oligomeric protein into a cell capable of expressing the natural oligomeric protein; and (b) a step of inhibiting the expression of the endogenous polypeptide.

In the second aspect of the present invention, the oligomeric protein may be composed of a variable region and a constant region, and the oligomeric protein may be an antigen recognition receptor, in particular, the antigen recognition receptor may be a TCR. Further, the expression of the endogenous polypeptide may be inhibited by RNA interference, and the oligomeric protein may be composed of a variable region and a constant region, and the expression of the endogenous polypeptide constituting the oligomeric protein may be inhibited by RNA interference targeting a sequence of an mRNA corresponding to a constant region of the polypeptide. Furthermore, the exogenous polypeptide may have a constant region of the same amino acid sequence as that of the endogenous polypeptide, and the expression of the endogenous polypeptide may be inhibited by making a nucleotide sequence of an mRNA of the exogenous polypeptide differ from a nucleotide sequence of an mRNA of the endogenous polypeptide.

The third aspect of the present invention relates to a method for forming a non-natural oligomeric protein, which comprises carrying out the following steps:

(a) a step of introducing a gene encoding an exogenous polypeptide constituting a non-natural oligomeric protein corresponding to at least one endogenous polypeptide constituting a natural oligomeric protein into a cell capable of expressing the natural oligomeric protein; and (b) a step of inhibiting the expression of the endogenous polypeptide.

In the third aspect of the present invention, the oligomeric protein may be composed of a variable region and a constant region, and the oligomeric protein may be an antigen recognition receptor, in particular, the antigen recognition receptor may be a TCR. Further, the expression of the endogenous polypeptide may be inhibited by RNA interference, and the oligomeric protein may be composed of a variable region and a constant region, and the expression of the endogenous polypeptide constituting the oligomeric protein may be inhibited by RNA interference targeting a sequence of an mRNA corresponding to a constant region of the polypeptide. Further, the exogenous polypeptide may have a constant region of the same amino acid sequence as that of the endogenous polypeptide, and the expression of the endogenous polypeptide may be inhibited by making a nucleotide sequence of an mRNA of the exogenous polypeptide differ from a nucleotide sequence of an mRNA of the endogenous polypeptide.

EFFECT OF THE INVENTION

According to the present invention, there is provided a cell expressing an oligomeric protein retaining the desired function at a high rate, in which at least one endogenous polypeptide is replaced with a exogenous polypeptide. The cell is extremely useful in treating diseases by cellular medical care.

BEST MODE FOR CARRYING OUT THE INVENTION

Figure 1:
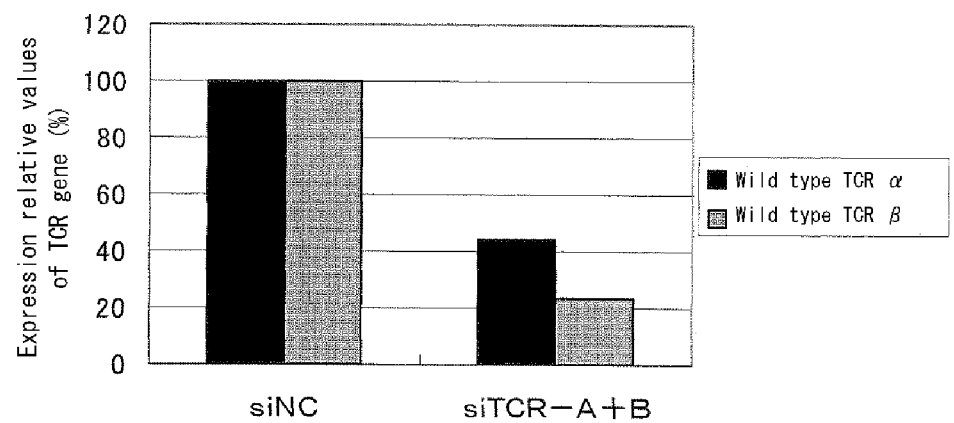
FIG. 1 is a view showing expression of a TCR gene.

The "oligomeric protein" as used herein means a protein composed of a plurality of constituent polypeptides (subunits). The oligomeric protein may be a homooligomer composed of a plurality of the same polypeptides, or a heterooligomer composed of a plurality of kinds of polypeptides. In addition, the number of polypeptides as constituent elements is not particularly limited, and the present invention can be applied to any of a dimer, a trimer, a tetramer, and an oligomer composed of a larger number of polypeptides. The oligomeric protein is formed via a covalent bond such as a disulfide bond (SS bond) between polypeptides, an electrostatic bond, etc.

The "endogenous polypeptide" as used herein means a polypeptide which is naturally expressed from an original gene intracellularly. To the contrary, the "exogenous polypeptide" means a polypeptide which has been artificially introduced from the outside, and examples thereof include a polypeptide which has been physically introduced into a cell, and a polypeptide expressed by a exogenous gene which is not originally present in the cell into which the polypeptide is introduced. In addition, the "non-natural oligomeric protein" is an oligomeric protein in which at least one endogenous polypeptide constituting the protein is replaced with a exogenous polypeptide, and includes any of an oligomeric protein composed of a exogenous polypeptide alone, and an oligomeric protein containing both of an endogenous polypeptide and a exogenous polypeptide. Although the present invention is not particularly limited, usually, a exogenous polypeptide has a different amino acid sequence from that of an endogenous polypeptide in such a range that an oligomeric protein can be formed.

The "inhibition of expression of a polypeptide" as used herein means inhibition of production of an eventual polypeptide by prohibition of transcription and/or translation from a gene encoding the polypeptide, that is, a decrease in the amount of a polypeptide as a product. Therefore, even when a transcription from a gene encoding a polypeptide is not inhibited, as long as a transcription product (mRNA) is rapidly degraded and production of a protein is inhibited, it is included in "inhibition of expression". In the present invention, expression of an endogenous polypeptide, expression of which is desired to be inhibited, is selectively inhibited.

A means for the "inhibition of expression of a polypeptide" is not particularly limited. Preferably, a means which can selectively inhibit expression of a polypeptide is used. For example, a means which inhibits expression of a polypeptide based on specificity to a steric structure or an amino acid sequence of the polypeptide, or a nucleotide sequence encoding the polypeptide is preferable in the present invention. The means is not particularly limited, and RNA interference, ribozyme, and antisense RNA which are means for inhibiting translation of a polypeptide from an mRNA are exemplified.

The "antigen recognition receptor" as used herein means a protein which specifically recognizes an antigen. As the antigen recognition receptor, a human-derived T cell receptor (TCR), and a TCR derived from an organism other than a human are exemplified. As the TCR, a heterodimer consisting of an α chain and a β chain, and a heterodimer consisting of a γ chain and a δ chain are known, and any of them can be preferably used in the present invention.

The "T cell" as used herein is also referred to as a T lymphocyte, and means a cell derived from the thymus among lymphocytes involved in an immunological response. Examples of the T cell include a helper T cell, a suppresser T cell, a controlling T cell, a CTL, a naïve T cell, a memory T cell, an αβ T cell expressing a TCR of an α chain and a β chain, and a γδ T cell expressing a TCR of a γ chain and a β chain. As a "cell population containing a T cell," cell populations including blood (peripheral blood, umbilical blood, etc.) or bone marrow liquid, a peripheral blood monocyte (PBMC), a hemocyte cell, a hematopoietic stem cell, or an umbilical blood monocyte which is collected, isolated, purified and induced from blood, bone marrow liquid, etc. are exemplified. In addition, various cell populations derived from hemocyte cells containing a T cell can be used in the present invention. These cells may be activated in vivo or exo vivo with a cytokine such as IL-2. As these cells, any of cells collected from a living body, or cells obtained through in vitro culturing, for example, a T cell population obtained by the method of the present invention as it is, or a population containing the T cell population which has been cryopreserved can be used.

In the following, the present invention will be explained specifically.

(1) The Cell of the Present Invention

The cell of the present invention is a cell which comprises an introduced gene encoding an exogenous polypeptide corresponding to at least one endogenous polypeptide constituting a natural oligomeric protein, wherein expression of the endogenous polypeptide is inhibited, whereby, a non-natural oligomeric protein can be expressed. By the above construction, the present invention has an advantage that a non-natural oligomeric protein having the desired function and containing a exogenous polypeptide as a constituent polypeptide is formed more efficiently as compared with the case where a exogenous polypeptide is simply expressed in a cell.

When a non-natural oligomeric protein to be expressed is a homooligomer, if expression of an endogenous polypeptide is inhibited by a proper expression inhibiting means, and a exogenous polypeptide is expressed, a ratio of formation of the desired non-natural oligomeric protein is improved. In the case of a heterooligomer, there are two cases: the case where the function of an oligomeric protein is altered by replacement of only one kind of the constituent polypeptide with a exogenous polypeptide; and the case where replacement of all of the constituent polypeptides with a exogenous polypeptide is necessary. In both cases, a treatment is carried out so that expression of an endogenous polypeptide corresponding to a exogenous polypeptide to be introduced, which is not desired to be incorporated into a desired non-natural oligomeric protein, is inhibited. For example, in the case where the desired function is exerted when a heterodimer as an oligomeric protein is formed with two kinds of exogenous polypeptides, expressions of two kinds of endogenous polypeptides corresponding to respective polypeptides are inhibited. In addition, when formation of a heterodimer consisting of one kind of a exogenous polypeptide and another kind of an endogenous polypeptide is desired, the expression of the endogenous polypeptide competing with the exogenous polypeptide is selectively inhibited.

In addition, the cell of the present invention may be a cell in which expression of an endogenous polypeptide is selectively inhibited as compared with expression of a exogenous polypeptide, and an expression level of an endogenous polypeptide as compared with the case of using no expression inhibiting means may be 20% or more, 40% or more, 60% or more, 80% or more or 100%, that is, the expression may be completely inhibited.

The oligomeric protein to which the present invention is applied is not particularly limited, but a structural protein, an enzyme, a transcription factor, a receptor, and an antibody are exemplified. In addition, in the present invention, the oligomeric protein may be a cell surface protein (membrane protein), and an application to an antigen recognition receptor, for example, a T cell receptor (TCR) exemplified in the Examples section is particularly preferable.

In the cell of the present invention, since expression of an endogenous polypeptide constituting a natural oligomeric protein is inhibited, competition between a exogenous polypeptide and an endogenous polypeptide is inhibited, and a proper oligomeric protein containing a exogenous polypeptide, expression of which is expected, is formed.

The cell used in the present invention is not particularly limited as long as the cell expresses an oligomeric protein, and any of an animal cell, a plant cell and a microorganism may be used. Since a T cell derived from a human or an animal other than a human expresses a TCR forming a heterodimer, the cell can be used in the present invention for the purpose of altering the TCR, although the purpose is not particularly limited. The cell of the present invention does not require deletion of a gene encoding an endogenous polypeptide or differentiation inducement which aims to make an endogenous polypeptide not expressed, at introduction of a exogenous polypeptide. That is, the present invention can employ a cell expressing an endogenous polypeptide and therefore it is useful.

In the present invention, as one aspect of a means for inhibiting expression of a polypeptide, RNA interference (RNAi) is utilized. RNA interference was reported in 1998, and has been attracting attention as a phenomenon of inhibition of gene expression due to degradation of a sequence-specific mRNA via a double-stranded RNA. The RNA interference is thought to occur by a mechanism wherein a long double-stranded RNA is degraded into a short RNA of 21 to 25 nucleotides referred to as an siRNA due to activity of an RNaseIII type called Dicer, subsequently, the siRNA is incorporated into a ribonucleic acid-protein complex referred to as a RISC (RNA-induced silencing complex), and this complex is bound to a target RNA ATP-dependently to degrade the target RNA.

In RNA interference in the present invention, for the purpose of selectively inhibiting expression of an endogenous polypeptide, an RNA molecule homologous with or complementary to a nucleotide sequence of an mRNA transcribed from a gene encoding an endogenous polypeptide, or a double-stranded RNA molecule including a chain of a sequence homologous with or complementary to a nucleotide sequence of the mRNA is utilized. Herein, the "homologous with or complementary to a nucleotide sequence of an mRNA transcribed from a gene encoding an endogenous polypeptide" and the "homologous with or complementary to a nucleotide sequence of an mRNA encoding an endogenous polypeptide" refer not only to be completely homologous with or complementary to a nucleotide sequence of an mRNA, but also to be substantially homologous or complementary in such a range that the desired function is exerted. In addition, the RNA molecule used in the present invention is referred to as an siRNA (short interfering RNA). The siRNA may be one kind of siRNA homologous with or complementary to one region of an mRNA transcribed from a gene encoding an endogenous polypeptide, or may be an siRNA including a plurality of double-stranded RNA molecules homologous with or complementary to a plurality of regions.

As the chain length of the siRNA used in the present invention, from the view point of inhibition of interferon response in a mammal cell, for example, an siRNA having a chain length of 13 to 29 bases, preferably an siRNA having a chain length of 15 to 25 base pairs and, further preferably, an siRNA having a chain length of 20 to 25 base pairs are exemplified. In addition, it is possible to use an siRNA in which all of the nucleotide sequence having the above chain length is derived from a nucleotide sequence of an mRNA of an endogenous polypeptide, or a part thereof is derived from the nucleotide sequence. Further, the siRNA used in the present invention, from the view point of effectiveness of RNA interference in a mammal cell, may be, for example, of a shape of a double-stranded RNA having a 2 to 4 bases single-stranded region protruding on a 3'-terminal side or, further preferably, of a shape of a double-stranded RNA having a 2 bases single-stranded region protruding on a 3'-terminal side. As the protruding single-stranded region, continuous deoxythymidine residues of 2 to 4 bases (TT, TTT, TTTT) are exemplified.

The siRNA used in the present invention is mainly composed of a ribonucleotide, and a part thereof may contain a deoxyribonucleotide, a derivative of a deoxyribonucleotide and/or a derivative of a ribonucleotide. The RNA of the present invention is not particularly limited, and can be synthesized by a known chemical synthesis method. Alternatively, the RNA may be enzymatically prepared (for example, using an RNA polymerase) with a proper template nucleic acid. The siRNA used in the present invention may be derived from a single-stranded RNA capable of forming a double strand in a molecule, and a single-stranded RNA of a stem-loop structure (short hairpin structure: sh structure) having a siRNA as a stem and optional sequences as a loop (shRNA) is exemplified. As the optional sequence, a sequence of 1 to 30 nucleotides is exemplified, and a sequence of preferably 1 to 25 nucleotides, further preferably 5 to 22 nucleotides can be used.

Concerning the siRNA used in the present invention, an siRNA or an RNA molecule containing an siRNA is directly introduced into a cell, or a nucleic acid construct from which the siRNA or the RNA molecule containing an siRNA is transcribed in a cell may be introduced in a cell. When the siRNA or the RNA molecule containing an siRNA is directly introduced into a cell, TransIT-TKO (manufactured by Mirus), or Human T Cell Nucleofector Kit (Amaxa) can be suitably used. On the other hand, when the nucleic acid construct from which the RNA molecule is transcribed is used, it is possible to use a construct in which a nucleic acid encoding the siRNA or the RNA containing an siRNA is linked to the downstream of a promoter capable of exerting the function in a mammal cell, in the state where the siRNA can be transcribed, that is, functionally, although the present invention is not particularly limited thereto. As a preferable aspect, there is exemplified a construct in which a nucleic acid encoding an RNA chain constituting a double-stranded RNA capable of inhibiting expression of a gene encoding an endogenous polypeptide is placed at the downstream of a promoter.

The promoter used in the nucleic acid construct is not particularly limited as long as it can function in a mammal cell, and examples thereof include an RNA polymerase II promoter, an RNA polymerase III promoter, and a promoter which can be regulated with tetracycline. In addition, it is advantageous to use a tissue-specific promoter because it becomes possible to specifically inhibit the function of an endogenous polypeptide in a desired cell, site or organ.

Examples of the RNA polymerase II promoter include, but are not limited to, a CMV promoter, etc. In addition, examples of the RNA polymerase III promoter include a tRNA promoter, a U6snRNA promoter, a histone H1 promoter, etc. Examples of the promoter which can be regulated with tetracycline include a tetracycline-regulated type U6 promoter, a TR promoter, etc. By combining the promoter with a Cre-lox P system, transcription of an RNA can be controlled more strictly.

The construction of the nucleic acid construct used in the present invention is not particularly limited. For example, the construct can be constructed so that sense and antisense chains of a double-stranded RNA capable of inhibiting the function of an objective gene are transcribed according to the following system: (A) a tandem type separately transcribing a sense RNA and an antisense RNA, in which a nucleic acid encoding a sense RNA and a nucleic acid encoding an antisense RNA are linked to the downstream of different two promoters, respectively, and the two transcription units are placed in a forward direction, (B) a type transcribing an RNA of a stem-loop type (or short hairpin type) in which a sense RNA and an antisense RNA are linked directly or via a loop, and in which a nucleic acid encoding a sense RNA and a nucleic acid encoding an antisense RNA are placed in the downstream of one promoter in a forward direction, or (C) an opposite type in which a promoter is placed on both ends of nucleic acids encoding a sense chain or an antisense chain in each strand, respectively, and both RNA chains are transcribed by separate promoters. In the present invention, the tandem type, the stem-loop type or the opposite type can be used selectively depending on the use conditions, for example, the kind of a mammal cell, and the kind of a sense sequence and an antisense sequence.

The nucleic acid construct used in the present invention may be incorporated into a suitable vector, for example, a plasmid vector or a virus vector so that it can exert the effect more stably in a cell. Furthermore, the nucleic acid construct of the present invention may be incorporated into a chromosomal DNA of a cell. The plasmid vector is not particularly limited, and examples thereof include a piGENE tRNA plasmid (trade name, manufactured by iGENE), siLentGene (manufactured by Promega), pSEC Hygro Vector (manufactured by Ambion), a pBAsi vector (manufactured by TAKARA BIO), etc., which express a nucleic acid for RNA interference. Examples of the virus vector include an adenovirus vector, an adeno-associated virus vector, a retrovirus vector, a lentivirus vector, etc. As an example of a commercially available adenovirus vector, Knockout Adenoviral RNAi System (manufactured by Clontech) is exemplified, and, as examples of a commercially available retrovirus vector, a pSINsi vector (manufactured by TAKARA BIO) and pSIREN-RetroQ Vector (manufactured by Clontech) are exemplified.

The prepared vector can be introduced into an objective cell according to a proper method suitable for the vector, for example, by an electroporation method, a lipofection method, etc. in the case of a plasmid vector, or by utilizing an ability of a virus to infect a cell in the case of a virus vector.

In the present invention, when a exogenous polypeptide contained in a non-natural oligomeric protein is present with an endogenous polypeptide corresponding to the exogenous polypeptide, they compete with each other for formation of an oligomeric protein and, at the same time, several kinds of oligomeric proteins containing the exogenous polypeptide or the endogenous polypeptide are formed. The exogenous polypeptide expressed in a cell of the present invention is not particularly limited as long as it is a polypeptide, whose expression is hardly inhibited with the expression inhibiting means used as compared with the endogenous polypeptide, preferably, a polypeptide whose expression is not inhibited. For example, when an siRNA is used as an expression inhibiting means, it is preferable that a gene encoding a exogenous polypeptide to be introduced is preferably of such a nucleotide sequence from which an RNA is transcribed does not have high homology with or complementarity to the siRNA, that is, of a sequence which does not receive an effect of the siRNA. When regions on RNAs on which an siRNA acts is the same between an endogenous polypeptide and a exogenous polypeptide, a nucleotide sequence of the exogenous polypeptide can be modified without changing an encoded amino acid sequence. It is known that there are 1 to 6 kinds of codons (combination of three bases) designating an amino acid on a gene, for every kind of an amino acid. By selecting a proper codon, a base can be modified without changing the encoded amino acid sequence (this modification is referred to as silent mutation). That is, the nucleotide sequence is different, but the amino acid sequence is the same. In the silent mutation, the third base of a codon is modified in many cases. When this silent mutation is introduced into a gene encoding a exogenous polypeptide, an siRNA inhibiting expression of an endogenous polypeptide does not act on an RNA transcribed from a gene encoding the exogenous polypeptide, and inhibition of the exogenous polypeptide expression is reduced. Thereby, expression of an endogenous polypeptide can be selectively inhibited as compared with expression of a exogenous polypeptide. In the present specification, a gene in which silent mutation is introduced as described above is called a "codon modified" gene in some cases, in the following. Upon the modification of a nucleotide sequence, by modification by selecting a codon frequently used in a host in which the codon is used, and a sequence increasing a translation efficiency, an improvement in an efficiency of expression of a exogenous polypeptide can be obtained, although the present invention is not limited thereto.

Further, in another aspect of inhibiting expression of an endogenous polypeptide with an siRNA, regarding an amino acid sequence of a exogenous polypeptide corresponding to a region of an RNA on which the siRNA acts, an amino acid sequence may be changed by substitution with another amino acid, for example, substitution with a similar amino acid in such a range that the function of a exogenous polypeptide is not impaired. The similar amino acid means an amino acid similar in the physicochemical nature, and examples thereof include amino acids classified into the same group, such as an aromatic amino acid (Phe, Trp, Tyr), an aliphatic amino acid (Ala, Leu, Ile, Val), a polar amino acid (Gln, Asn), a basic amino acid (Lys, Arg, His), an acidic amino acid (Glu, Asp), an amino acid having a hydroxyl group (Ser, Thr), an amino acid having a small side chain (Gly, Ala, Ser, Thr, Met), etc. It is expected that substitution with such a similar amino acid does not result in a change in a phenotype of a polypeptide (i.e. conservative amino acid substitution). Examples of the conservative amino acid substitution are well-known in the art, and disclosed in a variety of documents (for example, please see e.g. Bowie et al., Science, vol. 247, pp. 1306-1310 (1990)). By introducing conservative amino acid substitution into a exogenous polypeptide, an siRNA inhibiting the exogenous polypeptide expression of an endogenous polypeptide does not act on an RNA transcribed from a gene encoding the exogenous polypeptide, and inhibition of expression is reduced. Thereby, expression of an endogenous polypeptide can be selectively inhibited as compared with expression of a exogenous polypeptide.

As a T cell receptor (TCR), there are two kinds of TCRs including a heterodimer consisting of an α chain and a β chain, and a heterodimer consisting of a γ chain and a δ chain. Each chain of a TCR consists of a variable (V) region, a junction (J) region, and a constant (C) region. Diversity of the V region of a TCR occur due to a combination of gene segments encoding the V region, slippage of rearrangement binding sites, and insertion of an N sequence into a binding site upon rearrangement of a DNA. In a V region of an α chain and a β chain, a hypervariable region (CDR) in which occurrence of mutations in an amino acid sequence is particularly frequent is recognized.

As one aspect of the present invention, there is exemplified a T cell expressing a non-natural TCR, which comprises a introduced gene encoding a exogenous polypeptide constituting the non-natural TCR, wherein expression of an endogenous polypeptide corresponding to the exogenous polypeptide is inhibited. For example, when a TCR recognizing a desired antigen is introduced as a exogenous TCR into a T cell, in the T cell of the present invention in which expression of an endogenous TCR is inhibited, mispairing between a exogenous polypeptide and an endogenous polypeptide is decreased, thus, the number of molecules of a TCR heterodimer containing an objective exogenous polypeptide is increased. Further, since expression of the endogenous TCR is inhibited, among TCRs present on a cell surface, the ratio of a non-natural TCR is increased, and a monovalent T cell expressing only a non-natural TCR is increased. Therefore, specificity to an antigen is improved, which is advantageous in the field of cell therapy or the like. In addition, there is a possibility that upon introduction of a exogenous TCR into a cell expressing an endogenous TCR, gene expressions of the endogenous TCR and the exogenous TCR compete with each other, whereby, the expression of the exogenous TCR is reduced. Further, there is an additional possibility that a side effect such as graft-versus-host disease (GVHD), etc., due to the mispaired TCR may occur. The cell of the present invention can avoid a reduction in expression of the exogenous TCR, or side effects including GVDH.

An amino acid sequence of a V region of an endogenous TCR in each T cell differs from each other, while an amino acid sequence of a C region is suitable as a target of an siRNA since the amino acid sequence of the C region is encoded by a gene of the same nucleotide sequence which is a common sequence to individual T cells. Further, by modifying (substituting) a gene encoding a exogenous polypeptide in a region in which an siRNA acts on a gene encoding an endogenous polypeptide, that is, by obtaining the codon modified gene to render it a non-acting region, expression of an endogenous polypeptide is inhibited, thereby, expression of a exogenous polypeptide can be efficiently carried out.

For example, when expression of an endogenous TCR is inhibited, among a C region of a gene encoding a TCR, a nucleotide sequence AGTAAGGATTCTGATGTGTAT (SEQ ID No.: 19) of an endogenous α chain may be codon-modified into a nucleotide sequence AGCAAGGACAGC-GACGTGTAC (SEQ ID No.: 20) of a exogenous α chain, although the present invention is not limited thereto. Amino acid sequences encoded by the above two nucleotide sequences have a common region in SKDSDVY (SEQ ID No.: 21), but an α chain of an endogenous TCR is selectively inhibited by a double-stranded siRNA prepared by annealing RNAs shown as SEQ ID NO.: 3 and SEQ ID No.: 4. One example of a exogenous TCR α chain is a polypeptide encoded by a nucleotide sequence shown as SEQ ID No.: 1. In SEQ ID No.: 1, a nucleotide sequence of nucleotide 68 to 883 encode the TCR α chain. Among these, nucleotide 68 to 401 encode a V region, nucleotide 406 to 461 encode a J region, and nucleotide 462 to 883 encode a C region, respectively. Nucleotide 569 to 589 of SEQ ID No.: 1 corresponds to the SEQ ID No.: 20, and the sequence of the above region is different from that of an endogenous TCR α chain.

In addition, a nucleotide sequence GCCACCATCCTC-TATGAGATC (SEQ ID No.: 22) of an endogenous β chain may be codon-modified into a nucleotide sequence GCCAC-CATCCTGTACGAGATC (SEQ ID No.: 23) of a exogenous β chain. Amino acid sequences encoded by the above two nucleotide sequences have a common region in ATILYEI (SEQ ID No.: 24), but a β chain of an endogenous TCR is selectively inhibited by a double-stranded siRNA prepared by annealing RNAs shown as SEQ ID No.: 5 and SEQ ID No.: 6. One example of the exogenous TCR β chain is a polypeptide encoded by a nucleotide sequence described in SEQ ID No.: 2. In SEQ ID No.: 2, a nucleotide sequence of the nucleotide numbers 68 to 1006 encode a TCR β chain. Among these, nucleotide 68 to 414 encodes a V region, nucleotide 427 to 470 encodes a J region, and nucleotide 471 to 1006 encodes a C region, respectively. Nucleotide 902 to 922 of SEQ ID No.: 2 correspond to SEQ ID No.: 23, and the sequence of the above region is different from that of the endogenous TCR β chain.

A disease to which a T cell containing the introduced exogenous TCR of the present invention is administered is not particularly limited as long as it is a disease exhibiting sensitivity to the T cell, and examples of the disease include cancer (leukemia, solid tumor etc.), infectious diseases having a pathogen of a virus, a bacterium or a fungus, such as hepatitis, influenza, HIV, etc., for example, tuberculosis, MRSA, VRE, and deep mycosis. In addition, the cell of the present invention can be utilized for preventing an infectious disease after bone marrow transplantation or radiation irradiation, or in infusing a donor lymphocyte for the purpose of remission of recurrent leukemia.

In the present invention, a means for introducing a gene encoding a exogenous polypeptide is not particularly limited, and a suitable means can be selected for use from known gene introducing methods. Concerning the gene introducing method, any of a method using a virus vector, and a method not using the vector can be used. For details of those methods, many documents have been already published.

The virus vector is not particularly limited, and a known virus vector usually used in a gene introducing method, for example, a retrovirus vector (including a lentivirus vector, a pseudo type vector), an adenovirus vector, an adeno-associated virus vector, a simian virus vector, a vaccinia virus vector, a sendai virus vector, etc. is used. Particularly preferably, a retrovirus vector, an adenovirus vector, or a lentivirus vector is used. A virus vector which is deficient in the replicating ability so as not to self-replicate in an infected cell is suitable. Additionally, a substance improving a gene introduction efficiency such as RetroNectin (registered trade mark, manufactured by TAKARA BIO) can be used in gene introduction.

As the gene introducing method without using a virus vector, for example, a method using a carrier such as a liposome or ligand-polylysine, a calcium phosphate method, an electroporation method, a particle gun method, etc. can be used, although the present invention is not limited thereto. In this case, a exogenous gene incorporated into a plasmid DNA, a straight DNA or an RNA is introduced.

The retrovirus vector and the lentivirus vector can stably incorporate a exogenous gene inserted in the vector into a chromosomal DNA of a cell into which the vector is to be introduced, and are used for the purpose of a gene therapy or the like.

A gene encoding a exogenous polypeptide can be used wherein the gene is inserted into a vector or a plasmid so that the gene is expressed under control of a suitable promoter. Alternatively, in order to attain efficient transcription of a gene, another regulatory sequence cooperating with a promoter or a transcription initiation site, for example, an enhancer sequence or a terminator sequence, may be present in a vector. Alternatively, for the purpose of insertion into a chromosome of a T cell into which the gene is to be introduced by homologous recombination, for example, the gene may be placed between flanking sequences consisting of nucleotide sequences each having homology with nucleotide sequences on both sides of a desired target insertion site of a gene in the chromosome.

A nucleic acid used in the means for "inhibiting expression of a polypeptide", for example, a nucleic acid construct from which an siRNA or an RNA containing an siRNA is transcribed, and a gene encoding the exogenous polypeptide can be introduced into a cell separately, or can be introduced into a cell with a single vector.

(2) Process for Producing Cell, and Method for Forming Non-natural Oligomeric Protein, of the Present Invention A process for producing a cell, and a method for inhibiting oligomer formation composed of endogenous and exogenous polypeptides, of the present invention comprise the following steps:

(a) a step of introducing a gene encoding a exogenous polypeptide corresponding to at least one endogenous polypeptide constituting an oligomeric protein into a cell expressing the oligomeric protein; and (b) a step of inhibiting expression of the endogenous polypeptide.

The process for producing a cell of the present invention is the process for producing the cell of the present invention described in (1). Since a cell obtained by the process is reduced in interference with an endogenous polypeptide in formation of a non-natural oligomeric protein containing a exogenous polypeptide, a non-natural oligomeric protein having the desired function is efficiently formed as compared with the case where a exogenous polypeptide is simply expressed in a cell.

An order of the step (a) and the step (b) is not particularly limited and either of them may be the first. Alternatively, those steps may be carried out at the same time. A cell population containing the cell can be induced, cultured or isolated by adding a step of separating or isolating a cell with inhibited expression of an endogenous polypeptide to steps carried out in the process of the present invention, further, a process for producing a cell population containing these cells is also included in the process of the present invention. This separation or isolation step can be carried out with using expression of a exogenous polypeptide constituting a suitable non-natural oligomeric protein as an index.

In addition, a known protein or chemical component may be added to the steps of the process of the present invention and, for example, in the case of a T cell, cytokines, chemokines, and other components may be added. Herein, the cytokine is not particularly limited as long as it can act on and activate a T cell, and examples thereof include IL-2, IFN-γ, TGF-β, IL-15, IL-7, IFN-α, IL-12, CD40L, IL-27, etc. and, from the view point of enhancement of cellular immunity, particularly preferable examples include IL-2, IFN-γ, and IL-12. In addition, the chemokine is not particularly limited as long as it acts on a T cell and exhibits a migration activity, and examples thereof include RANTES, CCL21, MIP1α, MIP1β, CCL19, CXCL12, IP-10, or MIG.

EXAMPLES

The following examples further illustrate the present invention more specifically, but the present invention is not limited to the following examples.

In addition, fundamental operations of operations described herein were carried out according to the description of Molecular Cloning: A Laboratory Manual $3^{rd}$ ed., edited by T. Maniatis, et al., published by Cold Spring Harbor Laboratory in 2001.

Example 1

Preparation of Wild-type and Codon Modified Human T Cell Receptors' α and β Genes A codon modified human anti-MAGE-A4 TCR α gene was prepared by modifying a part of a wild-type gene. A nucleic acid fragment containing this gene was cloned into a KpnI-XhoI site of pPCR-Script (Stratagene). A sequence of a nucleic acid fragment containing a codon modified human anti-MAGE-A4 TCR α gene is shown as SEQ ID No.: 1 in Sequence Listing.

A codon modified human anti-MAGE-4 TCR β gene was prepared by modifying a part of a wild-type gene. A nucleic acid fragment containing this gene was cloned into a KpnI-XhoI site of pPCR-Script. A sequence of a nucleic acid fragment containing a codon modified human anti-MAGE-A4 TCR β gene is shown as SEQ ID No.: 2 in Sequence Listing.

Example 2

Confirmation of Gene Silencing Effect of siRNA in Human Peripheral Blood Mononuclear Cells A double-stranded siRNA for wild-type TCR α prepared by annealing SEQ ID Nos.: 3 and 4 (siTCR-A, 50 pmol) and a double-stranded siRNA for wild-type TCR β prepared by annealing SEQ ID Nos.: 5 and 6 (siTCR-B, 50 pmol) were mixed and introduced into a peripheral blood mononuclear cell (PBMC) separated from human peripheral blood using Human T Cell Nucleofector Kit (Amaxa) according to the procedure in the product manual. As a negative control, 100 pmol of an siRNA (siNC) prepared by annealing SEQ ID Nos.: 7 and 8 was introduced. Two days after from introduction, cells were recovered, and extraction of total RNA and DNaseI treatment were carried out with QIAGEN RNeasy Micro Kit (manufactured by Qiagen). The extracted total RNA was subjected to a reverse transcription reaction with M-MLV-RTase using a random primer (6 mer), and real time PCR was carried out using SYBR Premix Ex Taq and primers for amplifying wild-type TCR α of SEQ ID Nos.: 9 and 10, and primers for amplifying wild-type TCR β of SEQ ID Nos.: 13 and 14, and relative values of expression levels of wild-type TCR α and wild-type TCR β genes were calculated. Normalization of a total RNA amount was carried out using primers for amplifying β-actin genes of SEQ ID Nos.: 17 and 18.

By calculating ratios of expression relative values in each experimental group relative to expression relative values of wild-type TCR α and wild-type TCR β genes of a control experimental group, the gene silencing effects were evaluated. The results are shown in FIG. 1. In the drawing, the ordinate axis shows expression levels of wild-type TCR α and wild-type TCR β genes as relative values assuming values of a negative control as 100. The abscissa axis shows the introduced siRNA. As shown in FIG. 1, by introducing a double-stranded siRNA into wild-type TCR α and β, the silencing effects on expressions of wild-type TCR α and β genes were obtained.

Example 3

Figure 2:
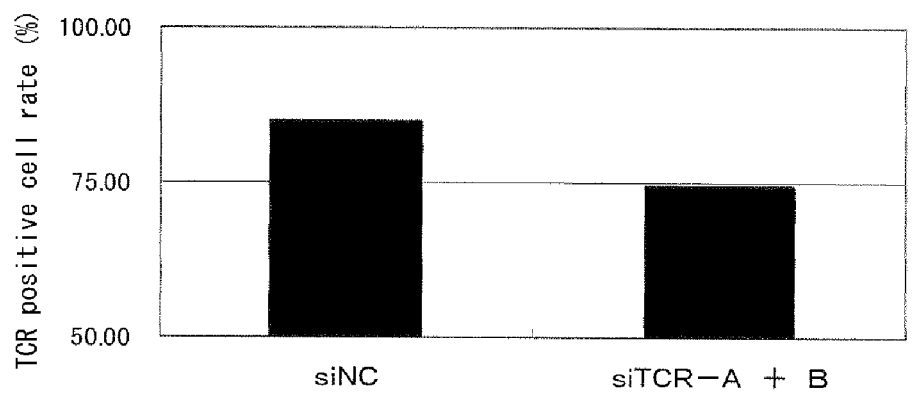
FIG. 2 is a view showing a TCR positive cell rate.
Figure 3:
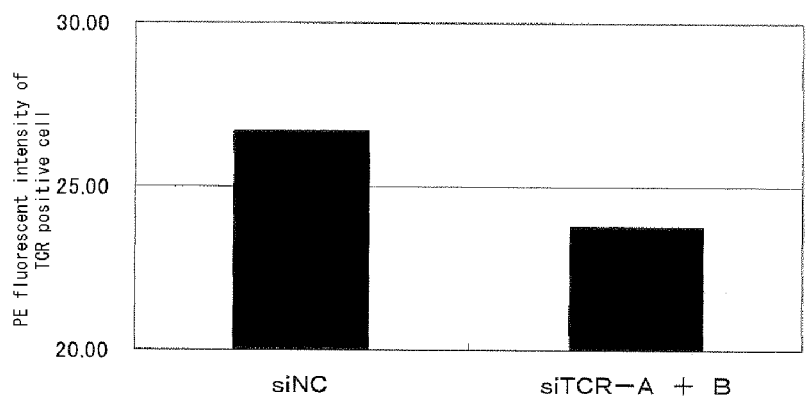
FIG. 3 is a view showing a fluorescent intensity of PE of a TCR positive cell.

Confirmation of Protein Expression Inhibiting Effect of siRNA in Human Peripheral Blood Mononuclear Cells The human peripheral blood mononuclear cells into which a double-stranded siRNA was introduced in Example 2 was stained with a PE-anti human TCR antibody (manufactured by BD Pharmingen) 3 days after introduction of a double-stranded siRNA, and a TCR positive cell ratio, and a fluorescent intensity of PE in TCR positive cells were measured by a flow cytometer. FIG. 2 shows TCR positive cell ratios, and FIG. 3 shows a fluorescent intensity of PE in TCR positive cells. The abscissa axis shows the introduced siRNAs. The ordinate axis shows a TCR positive cell ratio in FIG. 2, and shows a fluorescent intensity of PE in TCR positive cells in FIG. 3. As shown in FIGS. 2 and 3, by introducing double-stranded siRNAs for wild-type TCR α and β, reductions in the expression rate and the expression level of the endogenous wild-type TCR α/β complex protein of a human peripheral blood mononuclear cell was observed.

Example 4

Preparation of Codon Modified TCR Expression Retroviral Vector

First, PCR was carried out with a pPGK5 primer shown as SEQ ID No.:25 and a pPGK3 primer shown as SEQ ID No.: 26 employing a mouse genome as a template, and a DNA fragment containing a PGK promoter was obtained. This fragment was TA-cloned into a pT7 Blue vector (manufactured by MERCK).

Then, a PGK promoter site was cut out from this plasmid with NotI and BamHI, and cloned into a NotI and BamHI site of a pBlueScript-SK+ vector (manufactured by Stratagene) to prepare pBS-PPGK.

PCR was carried out with a 3MSCV5 primer shown as SEQ ID No.:27 and a 3MSCV3 primer shown as SEQ ID No.:28 using pMSCVneo (manufactured by Clontech) as a template to amplify a CMV3'LTR site, and the resulted fragment was cut with XhoI and EcoRI, and cloned into a Xho-EcoRI site of a pMT vector [a pM vector described in Gene Therapy, vol. 7, pp. 797-804 (2000)] to prepare pMSMC.

A codon modified TCR β gene was excised with PstI from the plasmid into which the codon modified TCR β gene in Example 1 was cloned, and cloned into a PstI site of pBS-PPGK to prepare pBS-Pb2.

Then, a PGK promoter +a modified TCR β gene were cut out from pBS-Pb2 with SacII and XhoI, and cloned into a SacII-XhoI site of pMSMC to prepare pMS-Pb2.

A codon modified TCR α gene was cut out from the plasmid into which the codon modified TCR α gene in Example 1 was cloned, and cloned into a NotI site of pMSMC to prepare pMS-Ma2.

Then, a codon modified TCR α gene was cut out from pMS-Ma2 with NotI, and cloned into a NotI site of pMS-Pb2 to obtain pMS-aPb1.

Escherichia coli JM109 was transformed with a plasmid vector pMS-aPb1, and the plasmid DNA was purified using a QIAGEN Plasmid Midi Kit (manufactured by Qiagen), and was used as a DNA for transfection.

The prepared pMS-aPb1 vector was introduced into a 293T cell using Retrovirus Packaging Kit Eco (manufactured by TAKARA BIO) according to the product protocol, various amphotropic virus supernatant were obtained, filtered with a 0.45 μm filter (Milex HV, manufactured by Millipore), and infected to PG13 cells (ATCC CRL-10686) with a method using polybrene, and the cell was cloned by a limiting dilution method. The culture supernatant of the resulting cloned cell was recovered, and filtered with a 0.45 μm filter, which was used as an MS-aPb1 codon modified TCR expression retrovirus solution.

Example 5

Infection of Human Peripheral Blood Mononuclear Cells with Codon Modified TCR Expression Retrovirus, and Introduction of siRNA The codon modified TCR expression retrovirus prepared in Example 4 was infected into a peripheral blood mononuclear cell (PBMC) separated from human peripheral blood two times according to a standard method using RetroNectin to prepare a modified TCR expression-introduced peripheral blood mononuclear cell. Three days after infection, 50 pmol of siTCR-A for wild-type TCR α and 50 pmol of siTCR-B for wild-type TCR β for which the gene silencing effects were confirmed in Examples 2 and 3 were mixed, and the mixture was introduced according to the procedure in the product manual. As a negative control, 100 pmol of siNC was introduced. Each 2 experimental groups were subjected. Two days after from introduction of siRNAs, cells were recovered, and extraction of total RNA and DNaseI treatment were carried out using QIAGEN RNeasy Micro Kit (manufactured by Qiagen). The extracted total RNA was subjected to a reverse transcription reaction with M-MLV-RTase (manufactured by TAKARA BIO) using a random primer (6 mer), real time PCR was carried out using SYBR Premix Ex Taq (manufactured by TAKARA BIO) and primers for amplifying wild-type TCR α of SEQ ID Nos.: 9 and 10, primers for amplifying codon modified TCR α of SEQ ID Nos.: 11 and 12, primers for amplifying wild-type TCR β of SEQ ID Nos.: 13 and 14, or primers for amplifying codon modified TCR β of SEQ ID Nos.: 15 and 16. Relative values of expression levels of wild-type TCR α, modified TCR α, wild-type TCR β and modified TCR β genes were calculated. Normalization of a total RNA amount was carried out using primers for amplifying a β-actin gene of SEQ ID Nos.: 17 and 18.

Figure 4:
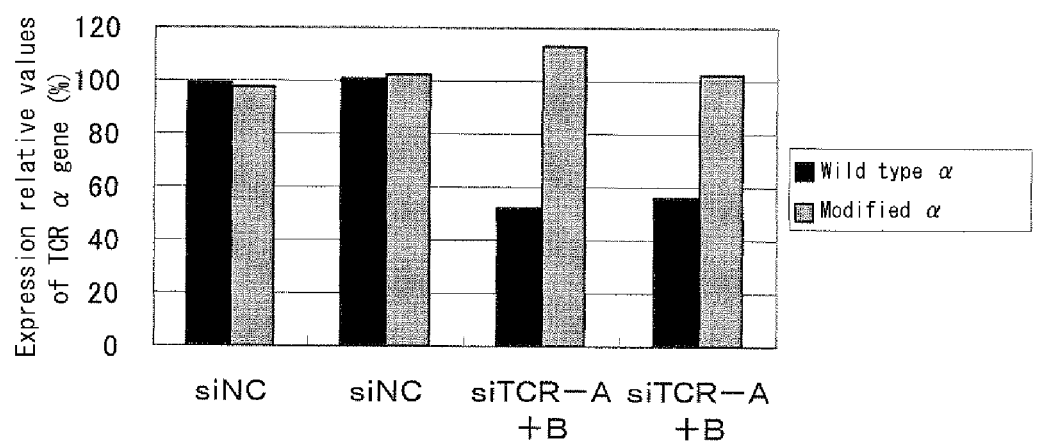
FIG. 4 is a view showing expression of a TCR α gene.
Figure 5:
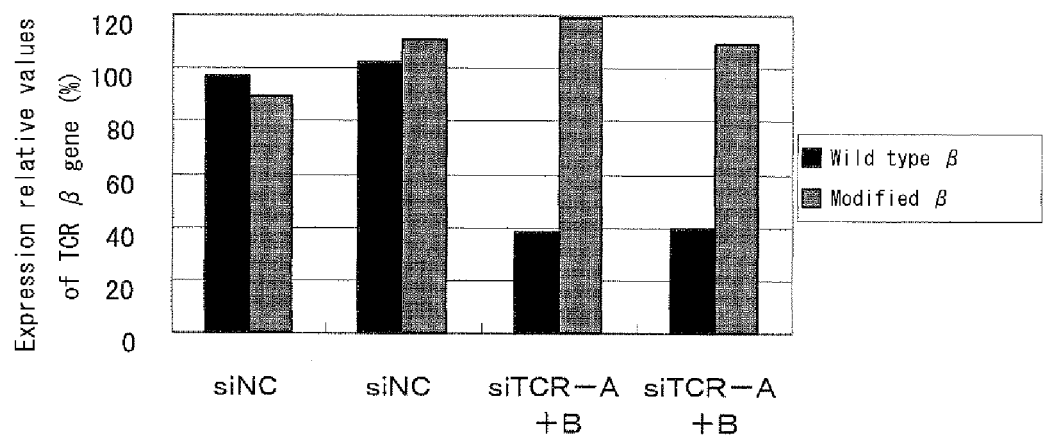
FIG. 5 is a view showing expression of a TCR β gene.

The gene silencing effect was evaluated by calculating ratios of expression relative values in each experimental group relative to expression relative values of wild-type TCR α, modified TCR α, wild-type TCR β and modified TCR β genes in a control experimental group. The results of TCR α are shown in FIG. 4, and the results of TCR β are shown in FIG. 5. In the drawings, the ordinate axis shows expression levels of wild-type TCR α, modified TCR α, wild-type TCR β and modified TCR β genes as relative values assuming values of a negative control as 100. The abscissa axis shows the introduced siRNAs. As shown in FIGS. 4 and 5, by introduction of double-stranded siRNAs for wild-type TCR α and β, expressions of wild-type TCR α and β genes are inhibited in PBMC, but inhibitions of expressions of modified TCR α and β genes does not occur.

Example 6

Figure 6:
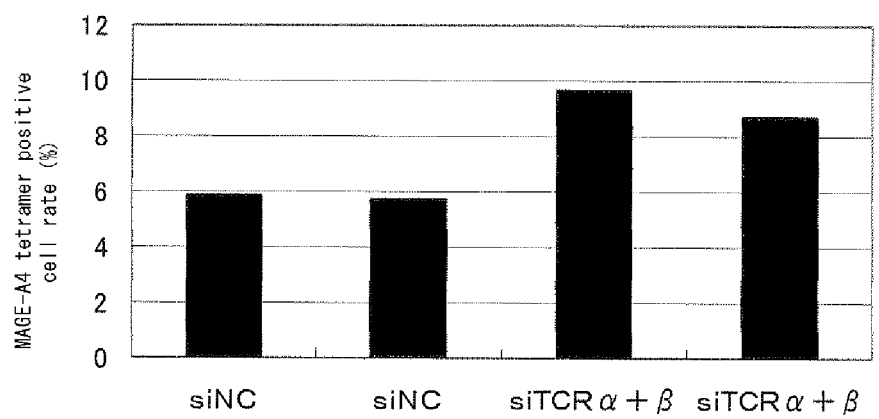
FIG. 6 is a view showing a MAGE-A4 tetramer positive cell rate.

Effect of Introduction of siRNA into Codon Modified TCR-introduced Human Peripheral Blood Mononuclear Cells on Expression of Codon Modified TCR Protein Three days after introduction of siRNA into a human peripheral blood mononuclear cell into which a codon modified TCR had been introduced in Example 5, the cells were stained with HLA-A2402 MAGE-A4 tetramer-PE (manufactured by MBL) and Human CD8 TRI-COLOR CONJUGATE (CALTAG Laboratories), and a ratio of CD8-positive and tetramer-positive cells was measured by a flow cytometer. Each 2 experimental groups were subjected. FIG. 6 shows a MAGE-A4 tetramer positive cell ratio. The abscissa axis shows the introduced siRNA, and the ordinate axis shows a MAGE-A4 tetramer positive cell ratio. As shown in FIG. 6, by introduction of a double-stranded siRNAs for wild-type TCR α and β, enhancement of an expression rate of a modified anti-MAGE-A4 TCR α/β complex protein whose gene was introduced into a human peripheral blood mononuclear cell was observed.

Example 7

Preparation of Codon Modified TCR and siRNA Coexpression Retroviral Vector

A double-stranded DNA prepared by annealing SEQ ID Nos.: 29 and 30 was cloned into a BamHI-ClaI site of a pSINsi-hU6 vector (manufactured by TAKARA BIO) to prepare pSINsi-hU6-TCRA. Separately, a double-stranded DNA prepared by annealing SEQ ID Nos.: 31 and 32 was cloned into a BamHI-HindIII site of a pBAsi-mU6 vector (manufactured by TAKARA BIO) to prepare pBAsi-mU6-TCRB.

Figure 7:
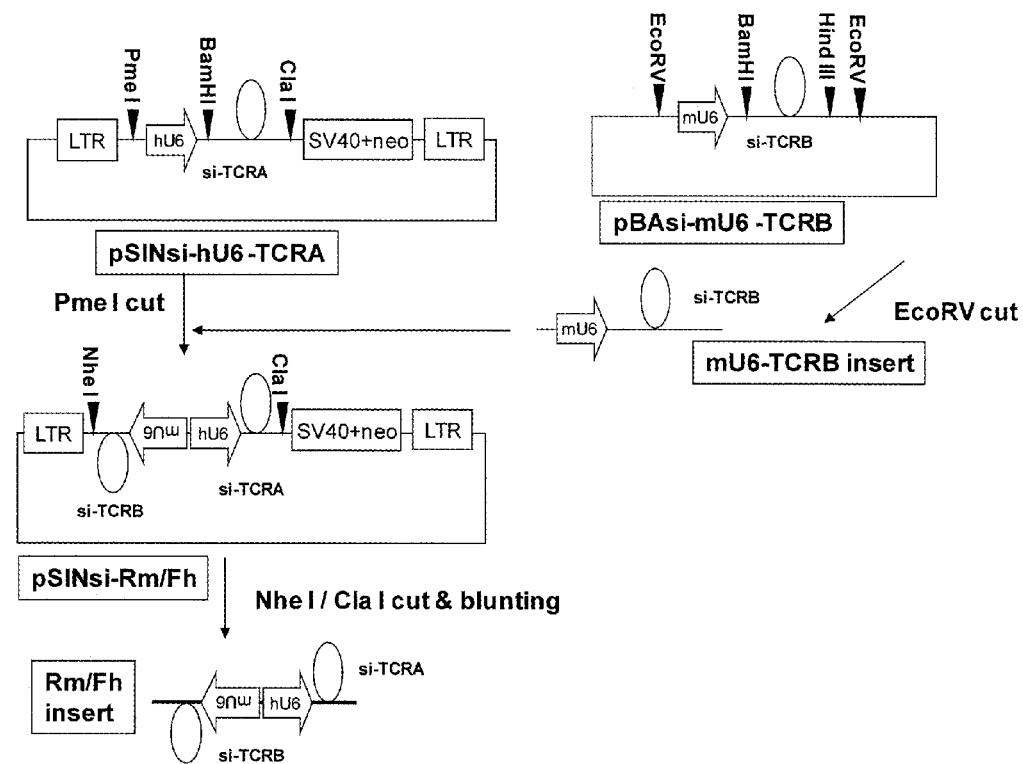
FIG. 7 is a view showing a flow chart of Rm/Fh insert construction.

As shown in FIG. 7, the prepared pBAsi-mU6-TCRB was cut out with EcoRV to obtain an mU6-TCRB insert, which was cloned into a PmeI site of pSINsi-hU6-TCRA to obtain pSINsi-Rm/Fh. The prepared pSINsi-Rm/Fh was digested with NheI and ClaI, and both ends were blunted to obtain an Rm/Fh insert.

Figure 8:
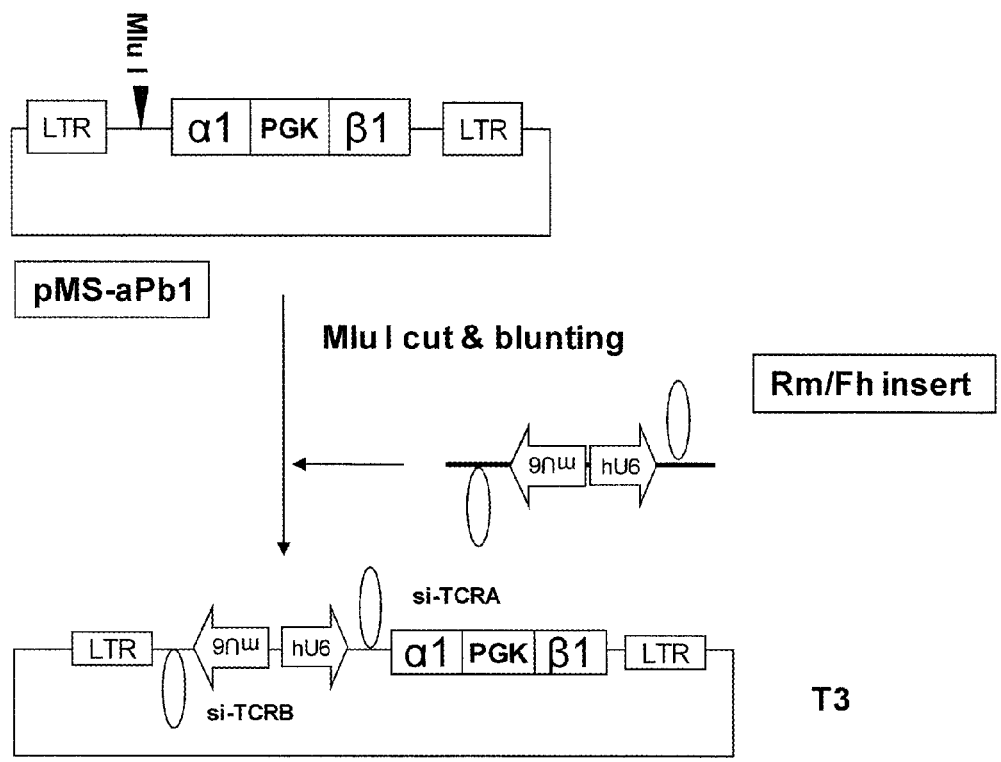
FIG. 8 is a view showing a flow chart of T3 vector construction.

As shown in FIG. 8, the pMS-aPb1 vector prepared in Example 4 was digested with MluI, both ends was blunted, and the Rm/Fh insert was cloned therein to prepare a T3 vector.

Figure 9:
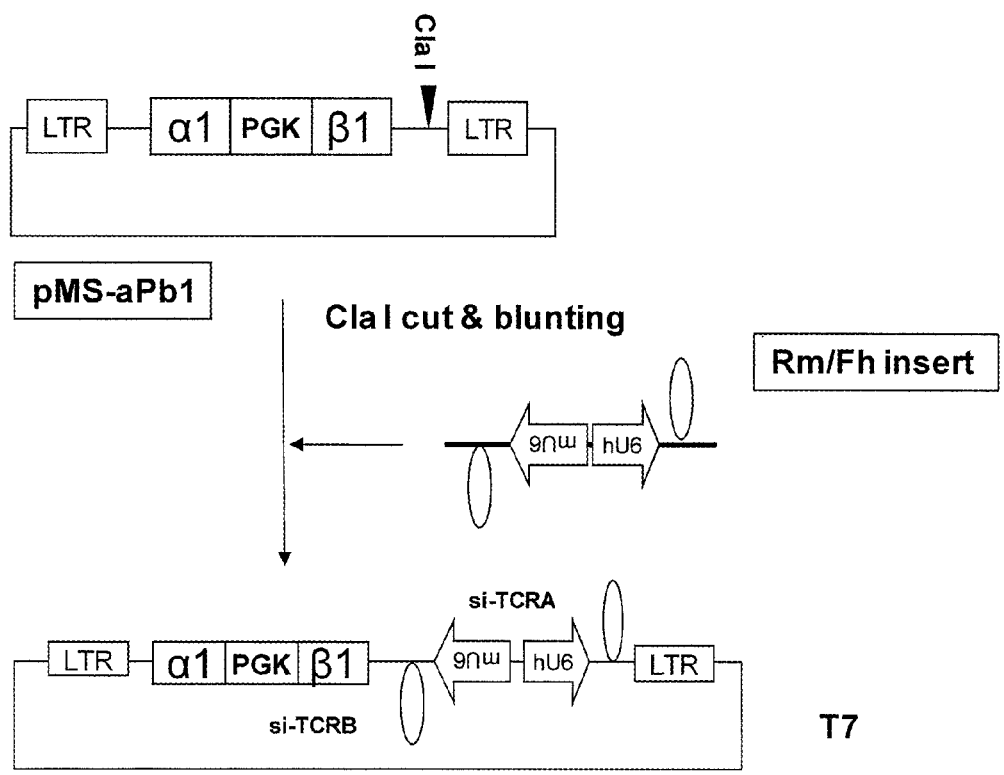
FIG. 9 is a view showing a flow chart of T7 vector construction.

In addition, as shown in FIG. 9, the pMS-aPb1 vector prepared in Example 4 was digested with ClaI, both ends were blunted, and the Rm/Fh insert was cloned therein to prepare a T7 vector.

Figure 10:
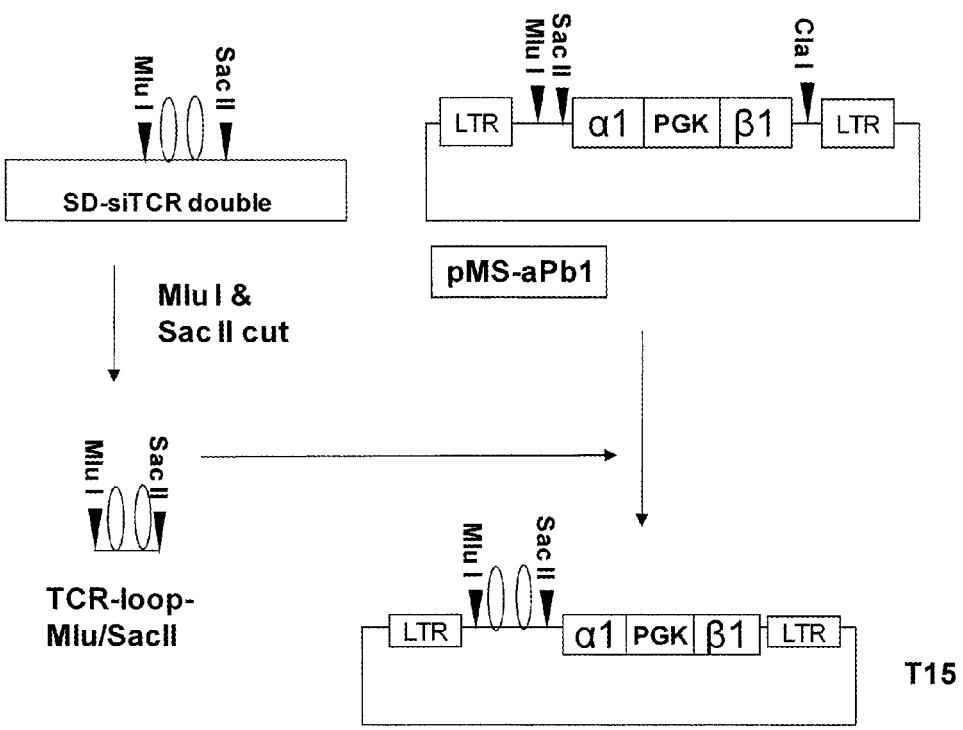
FIG. 10 is a view showing a flow chart of T15 vector construction.

Then, as shown in FIG. 10, an artificially synthesized gene shown as SEQ ID No.: 33 was digested with MluI and SacII to obtain TCR-loop-MluI/SacII, which was cloned into an MluI-SacII site of the pMS-aPb1 prepared in Example 4 to obtain a T15 vector.

Figure 11:
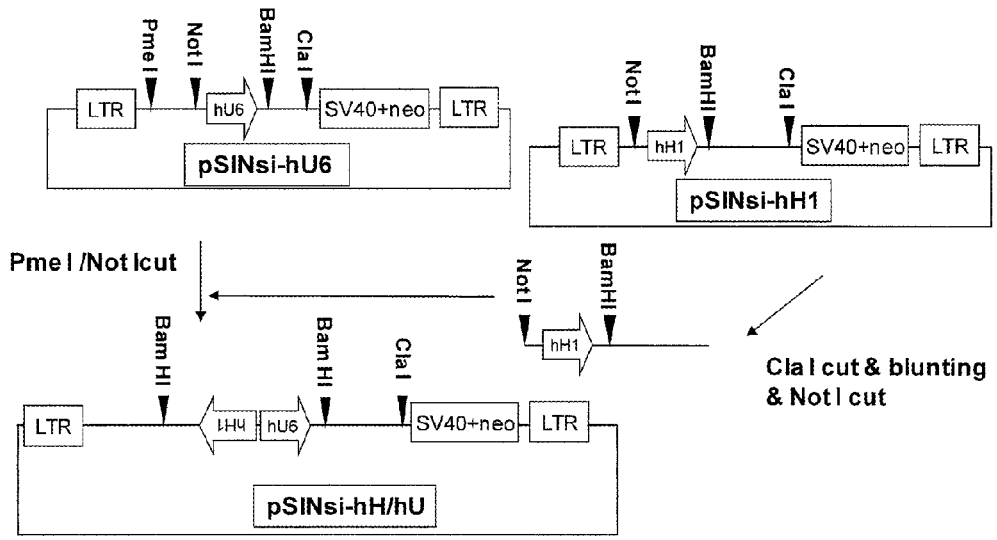
FIG. 11 is a view showing a flow chart of pSINsi-hH/hU construction.

Further, as shown in FIG. 11, a pSINsi-hH1 vector (manufactured by TAKARA BIO) was digested with ClaI, subjected to end blunting, and digested with NotI to obtain a fragment, which was cloned into a PmeI-NotI site of pSINsi-hU6 (manufactured by TAKARA BIO) to prepare pSINsi-hH/hU.

Figure 12:
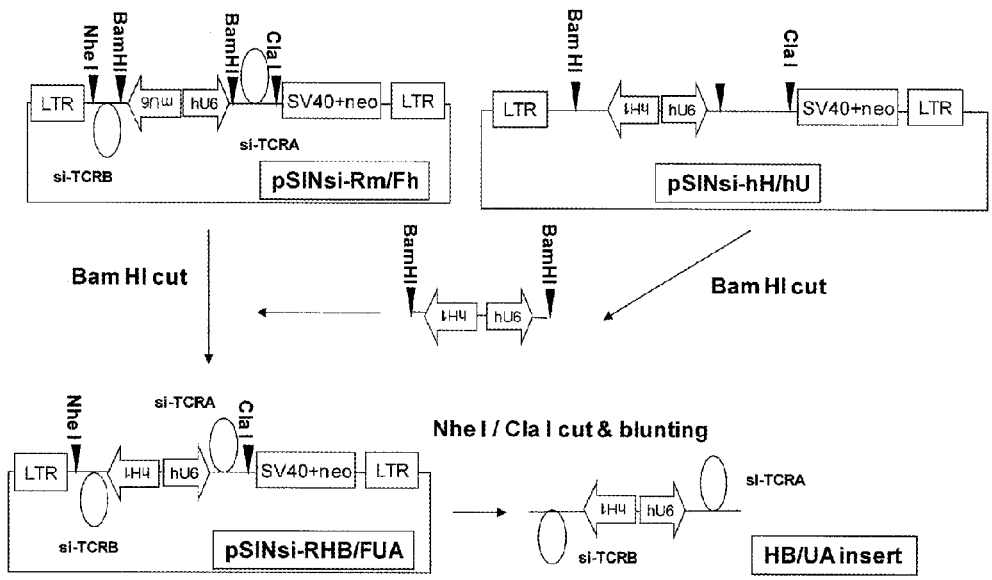
FIG. 12 is a view showing a flow chart of HB/UA insert construction.

As shown in FIG. 12, the pSINsi-hH/hU was digested with BamHI to obtain a fragment, which was cloned into a site obtained by digesting the pSINsi-Rm/Fh with BamHI to prepare pSINsi-RHB/FUA, and this was digested with NheI and ClaI, and subjected to end blunting to obtain an HB/UA insert.

Figure 13:
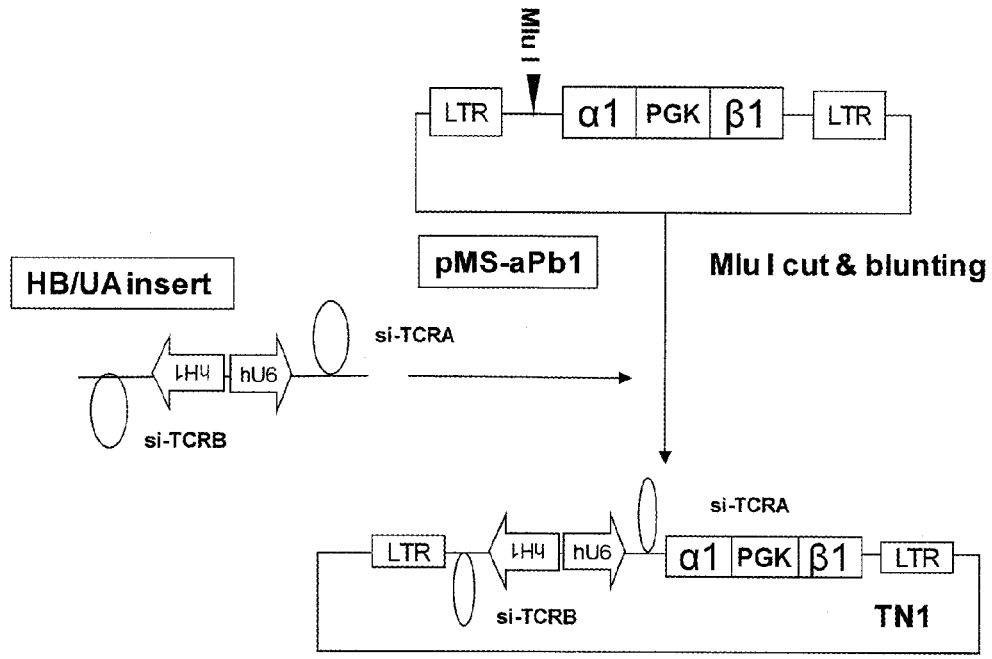
FIG. 13 is a view showing a flow chart of TN1 vector construction.

As shown in FIG. 13, the pMS-aPb1 vector prepared in Example 4 was digested with MluI, and subjected to end blunting, and an HB/UA insert was cloned therein to prepare a TN1 vector.

Figure 14:
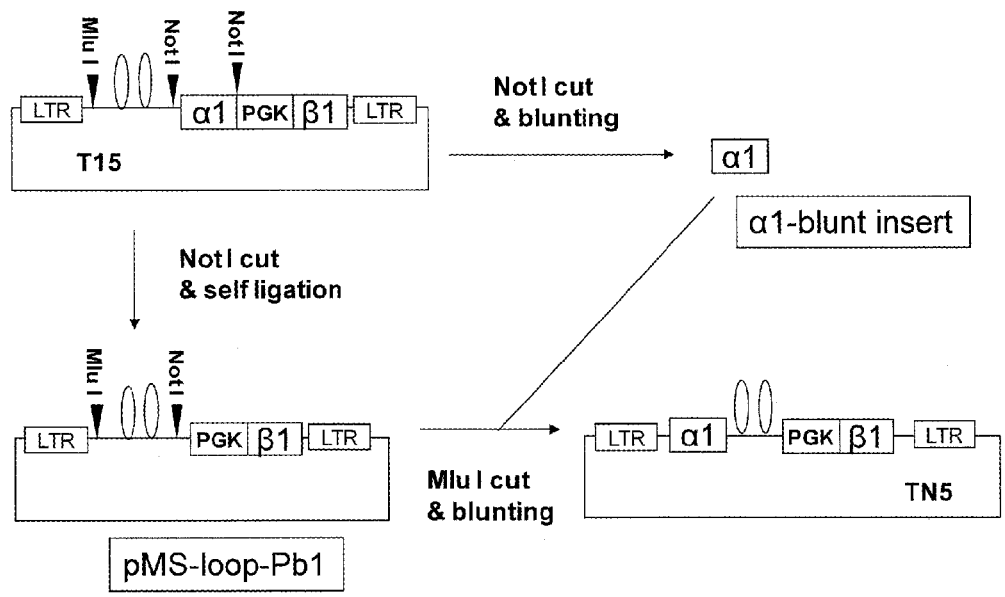
FIG. 14 is a view showing a flow chart of TN5 vector construction.

As shown in FIG. 14, a T15 vector was digested with NotI, and subjected to end blunting to make an a1-blunt insert. Separately, the T15 vector was digested with NotI, a pMS-loop-Pb1 vector obtained by self-ligation of a vector was digested with MluI, and the a1-blunt insert was cloned into an end-blunted site, thereby, a TN5 vector was prepared.

Figure 15:
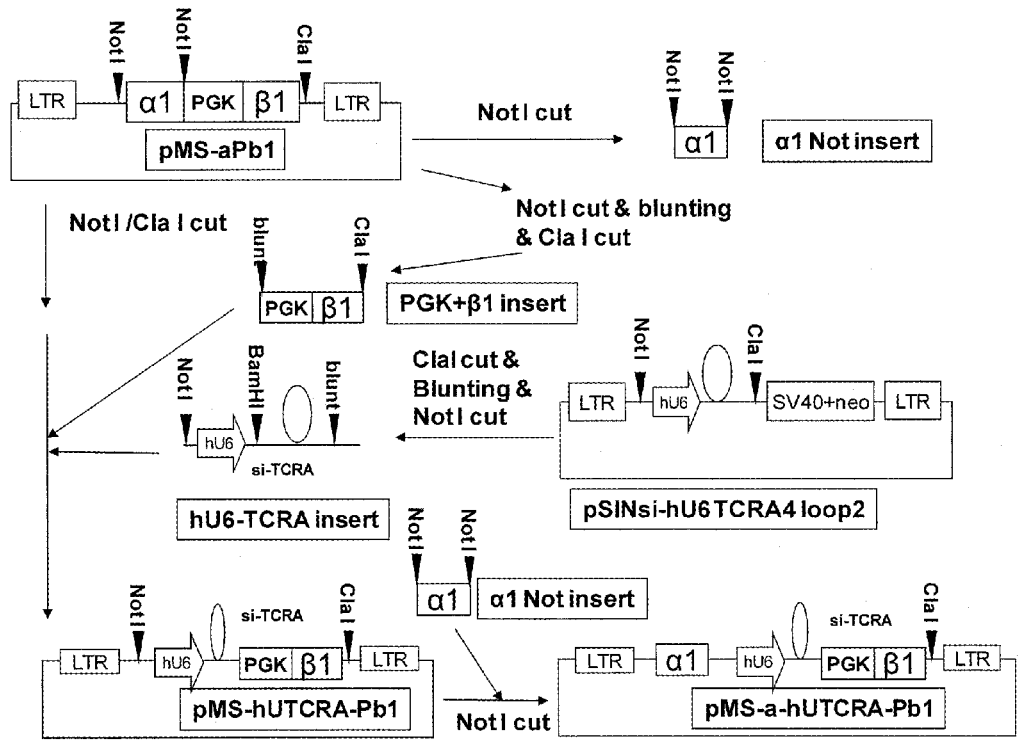
FIG. 15 is a view showing a flow chart of pMS-a-hUT-CRA-Pb1 construction.

As shown in FIG. 15, the pMS-aPb1 vector prepared in Example 4 was digested with NotI to make an a1 Not insert. Separately, the pMS-aPb1 vector was digested with NotI, subjected to end blunting, and digested with ClaI to prepare a PGK+β1 insert. Further, the pSINsi-hU6-TCRA vector was digested with ClaI, subjected to end blunting, and digested with NotI to obtain an hU6-TCRA insert. The PGK+β1 insert and the hU6-TCRA insert were cloned into a NotI-ClaI site of the pMS-aPb1 to prepare pMS-hURA-Pb1, this was digested with NotI, and the a1 Not insert was cloned therein to prepare pMS-a-hUTCRA-Pb1.

Figure 16:
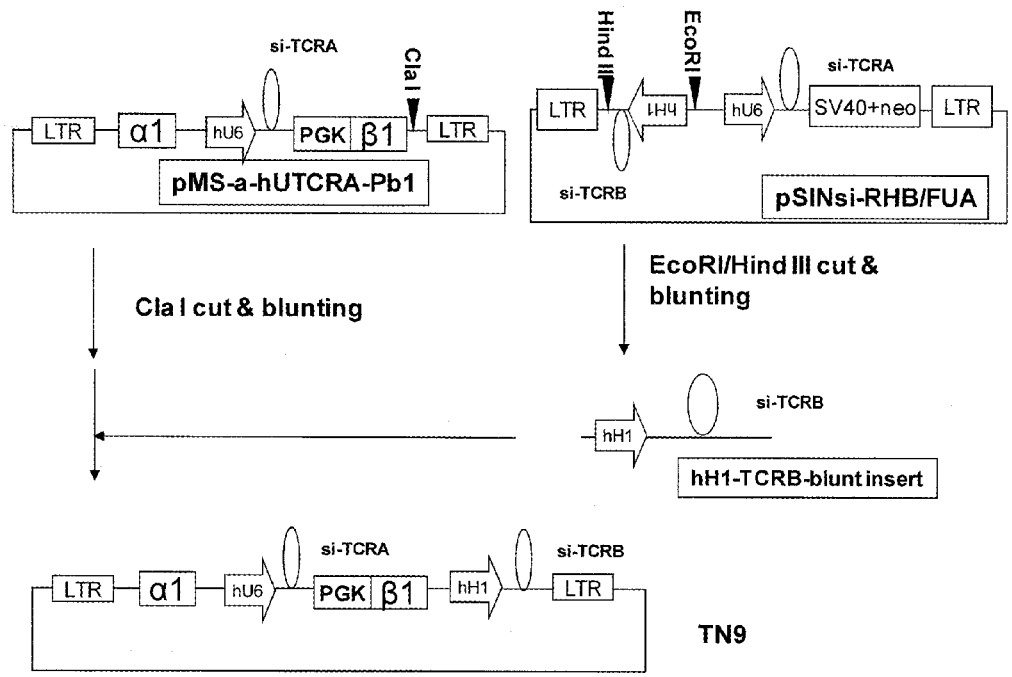
FIG. 16 is a view showing a flow chart of TN9 vector and TN11 vector construction.

As shown in FIG. 16, pSINsi-RHB/FUA was digested with EcoRI and HindIII, and subjected to end blunting to obtain an hH1-TCRB-blunt insert. The pMS-a-hUTCRA-Pb1 was digested with ClaI, and subjected to end blunting, and the hH1-TCRB-blunt insert was cloned therein to prepare a TN9 vector and a TN11 vector.

*Escherichia coli* JM109 was transformed with a plasmid vector, a pMS-aPb1, T3, T7, T15, TN1, TN5 or TN9 vector, and the plasmid DNA was purified using QIAGEN Plasmid Midi Kit (manufactured by Qiagen) to provide a DNA for transfection.

A 293T cell was transfected with the prepared pMS-aPb1, T3, T7, T15, TN1, TN5 or TN9 vector using Retrovirus Packaging Kit Eco (manufactured by TAKARA BIO) according to the product protocol, various amphotropic virus supernatants were obtained, filtered with a 0.45 μm filter (Milex HV, manufactured by Millipore), and was infected on a PG13 cell (ATCC CRL-10686) with a method using polybrene, and the culture supernatant of a cell was recovered, and filtered with a 0.45 μm filter to obtain an MS-aPb1, T3, T7, T15, TN1, TN5 or TN9 retrovirus solution.

Example 8

Infection of Human Peripheral Blood Mononuclear Cells with Codon Modified TCR and siRNA Coexpression Retrovirus Vector 1

A peripheral blood mononuclear cell (PBMC) separated from human peripheral blood was infected two times with the T3, T7, or T15 codon modified TCR and siRNA coexpression retrovirus prepared in Example 7 as well as a codon modified TCR expression pMS-aPb1 vector as a control according to a standard method using RetroNectin to prepare a codon modified TCR and siRNA coexpression-introduced peripheral blood mononuclear cell. Three days after second virus infection, cells were recovered, and extraction of total RNA and DNaseI treatment were carried out with QIAGEN RNeasy Mini Kit (manufactured by Qiagen). The extracted total RNA was subjected to a reverse transcription reaction with PrimeScript RT regent Kit (Perfect Real Time) (manufactured by TAKARA BIO), real time PCR was carried out using SYBR Premix Ex TaqII (manufactured by TAKARA BIO), primers for amplifying wild-type TCR α of SEQ ID Nos.: 9 and 10, primers for amplifying codon modified TCR α of SEQ ID Nos.: 11 and 12, primers for amplifying wild-type TCR β of SEQ ID Nos.: 13 and 14, and primers for amplifying codon modified TCR β of SEQ ID Nos.: 15 and 16, and relative values of expression levels of wild-type TCR α, modified TCR α, wild-type TCR β and modified TCR β genes were calculated. Normalization of a total RNA amount was carried out using primers for amplifying GAPDH genes of SEQ ID Nos.: 34 and 35.

Figure 17:
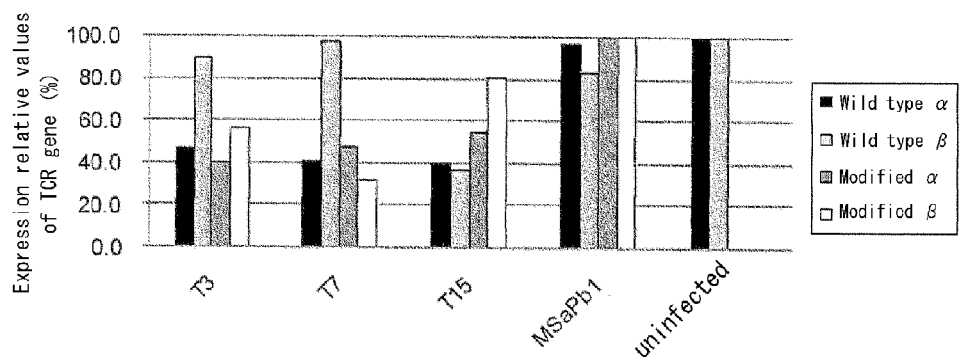
FIG. 17 is a view showing expression of a TCR gene.

By calculating ratios of expression relative values in each experimental group relative to expression relative values of wild-type TCR α, modified TCR α, wild-type TCR β and modified TCR β genes in a control experimental group, the wild-type TCR gene inhibiting effects and expression levels of modified TCR genes were evaluated. The results are shown in FIG. 17. In the drawing, the ordinate axis shows expression levels of wild-type TCR α, modified TCR α, wild-type TCR β and modified TCR β genes as relative values, assuming a values of a negative control without gene introduction as 100. The abscissa axis shows the introduced retrovirus. As shown in FIG. 17, by introducing an siRNA for wild-type TCR α and β, expression of wild-type TCR α and β genes is inhibited in PBMC. Expression of modified TCR α and β genes is lower in T3, T7 and T15 as compared with pMS-aPb1.

Example 9

Effect of Introduction of Codon Modified TCR and siRNA Coexpression Retroviral Vector on Expression of Codon Modified TCR Protein 1

Figure 18:
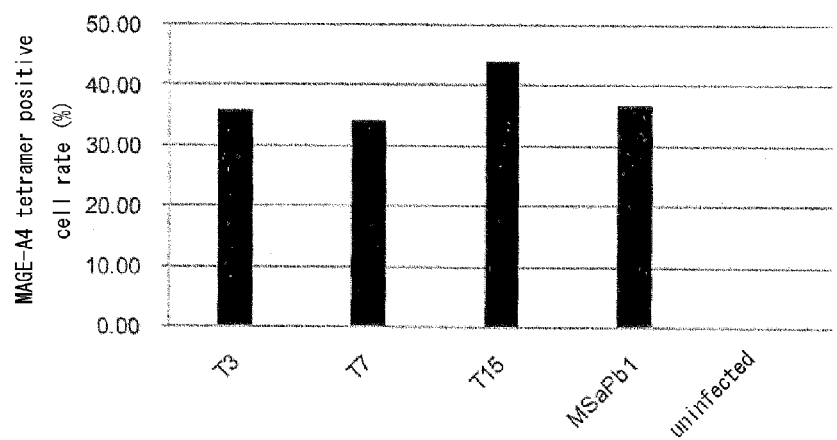
FIG. 18 is a view showing a MAGE-A4 tetramer positive cell rate.

In Example 8, three days after from second infection with a T3, T7 or T15 codon modified TCR and siRNA coexpression retrovirus, cells were recovered, and a ratio of CD8-positive and tetramer-positive cells was measured according to the same method as that of Example 6. FIG. 18 shows a MAGE-A4 tetramer positive cell ratio. The abscissa axis shows the introduced retrovirus, and the ordinate axis shows a MAGE-A4 tetramer positive cell ratio. As shown in FIG. 18, by introduction of the T15 codon modified TCR and siRNA coexpression retroviral vector, an expression rate of the modified anti-MAGE-A4 TCR α/β complex protein whose genes had been introduced into a human peripheral blood mononuclear cell was improved as compared with the codon modified TCR expression pMS-aPb1 as a control. As shown in Example 8, by insertion of the siRNA expression unit, although an expression level of the codon modified TCR gene was lower as compared with pMS-aPb1, enhancement of an expression rate of the codon modified anti-MAGE-A4 TCR α/β complex protein due to the effects of the siRNAs on inhibiting expression of the wild-type TCR gene was observed.

Example 10

Infection of Codon Modified TCR and siRNA Coexpression Retroviral Vector on Human Peripheral Blood Mononuclear Cells 2

Using a peripheral blood mononuclear cell (PBMC) separated from human peripheral blood, a codon modified TCR and siRNA coexpression-introduced peripheral blood mononuclear cell was prepared as in Example 8. After 7 days from virus infection, extraction of total RNA and DNaseI treatment were carried out. Real time PCR was carried out according to the same method as that of Example 8, and relative values of expression levels of wild-type TCR α, modified TCR α, wild-type TCR β, and modified TCR β genes were calculated.

Figure 19:
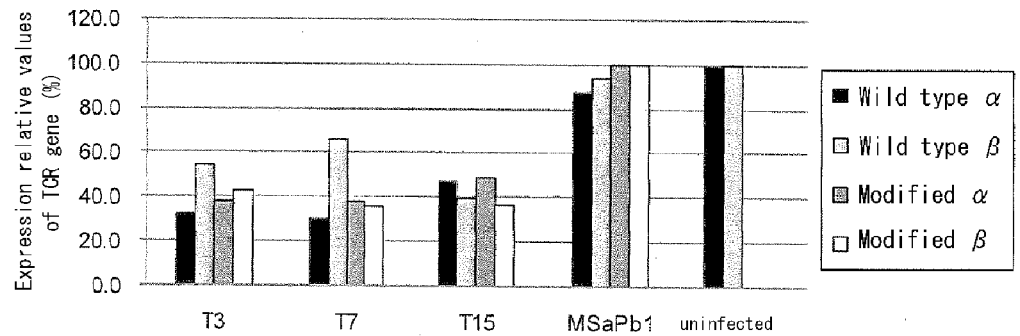
FIG. 19 is a view showing expression of a TCR gene.

By calculating ratios of expression relative values in each experimental group relative to an expression relative values of wild-type TCR α, modified TCR α, wild-type TCR β, and modified TCR β genes in a control experimental group, the wild-type TCR gene silencing effects and expression levels of the modified TCR gene were evaluated. The results are shown in FIG. 19. In the drawing, the ordinate axis shows expression amounts of wild-type TCR α, modified TCR α, wild-type TCR β, and modified TCR β gene as relative values, assuming values of a negative control without gene introduction as 100. The abscissa axis shows the introduced retrovirus. As shown in FIG. 19, by expressions of siRNAs for wild-type TCR α and β, expressions of the wild-type TCR α and β genes are inhibited in PBMC. In addition, the effects on inhibiting expressions of the wild-type TCR genes are higher on the $7^{th}$ day from virus infection than the results of Example 8 on the $3^{rd}$ day from virus infection. However, by insertion of siRNA expression unit for the wild-type, expression of the modified TCR α and β genes is lower as compared with pMS-aPb1.

Example 11

Effect of Introduction of Codon Modified TCR and siRNA Coexpression Retroviral Vector on Expression of Codon Modified TCR Protein 2

Figure 20:
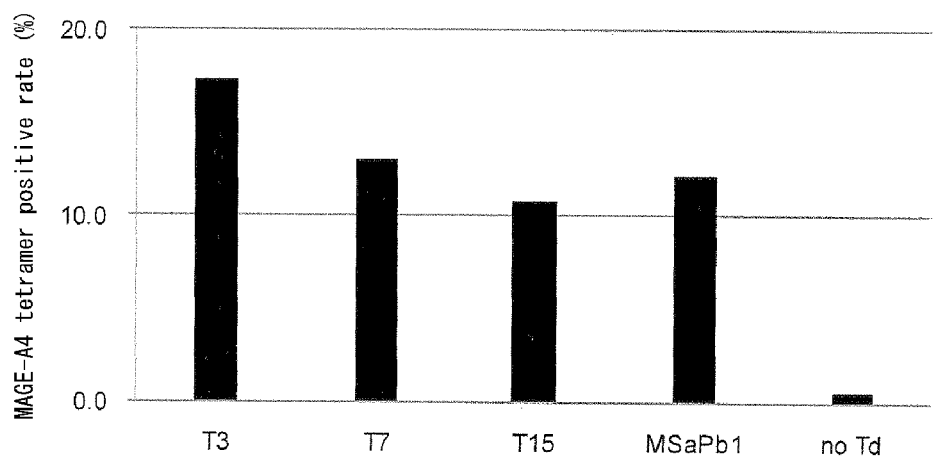
FIG. 20 is a view showing a MAGE-A4 tetramer positive cell rate.

In Example 10, after 7 days from second infection with a T3, T7 or T15 codon modified TCR and siRNA coexpression retrovirus, cells were recovered, and a ratio of cells which are CD8-positive and tetramer-positive was measured according to the same method as that of Example 6. FIG. 20 shows a MAGE-A4 tetramer positive cell ratio. The abscissa axis shows the introduced retrovirus, and the ordinate axis shows a MAGE-A4 tetramer positive cell rate. As shown in FIG. 20, by introduction of the T3 or T7 codon modified TCR and siRNA coexpression retroviral vector, an expression rate of the modified anti-MAGE-A4 TCR α/β complex protein whose genes had been introduced into a human peripheral blood mononuclear cell was improved as compared with the codon modified TCR expression pMS-aPb1 as a control. As shown in Example 10, by insertion of the siRNA expression unit, although an expression level of the codon modified TCR gene was reduced, enhancement of an expression rate of the codon modified anti-MAGE-A4 TCR α/β complex protein was observed due to the effect of inhibiting expression of the wilt-type TCR gene by an siRNA.

Example 12

Antigen-Specific Cytokine Producing Ability of Codon Modified TCR Complex Due to Introduction of Codon Modified TCR and siRNA Coexpression Retroviral Vector 1

Figure 21:
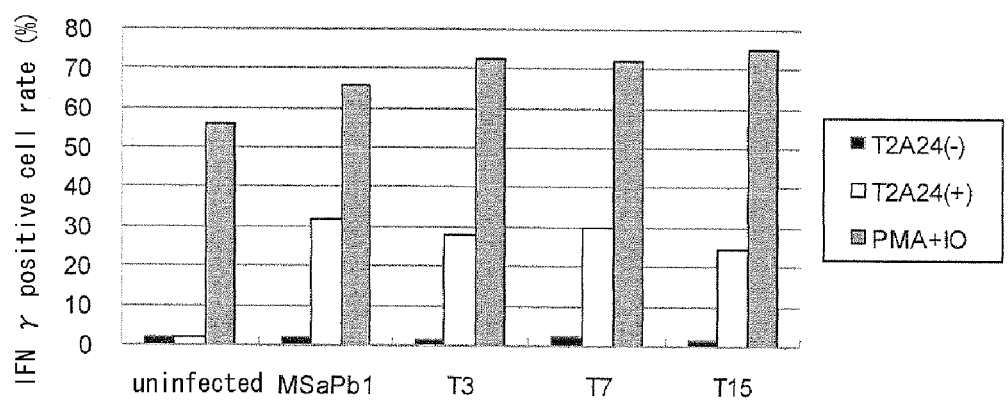
FIG. 21 is a view showing an intracellular IFN γ positive cell rate.

After Breferdin A was added to a cell mixture of a T2A24 (+) cell obtained by pulsing a T2A24 cell prepared by gene-introducing a HLA-A2402 cDNA into a T2 cell strain (ATCC CRL-1992) with a MAGE-A4$_{143-151}$ peptide or a T2A24 (−) cell without pulsing the T2A24 cell with the peptide, and a cell after 3 days from introduction of T3, T7, T15 or MS-aPb1 in Example 10, and a cell after 3 days from introduction of T3, T7, T15 or MS-aPb1 in Example 10, antigen-non-specifically stimulated with PMA and ionomycin, the resulted cells were incubated at 37° C. overnight, CD8 staining and intracellular IFN γ staining were carried out with a CD8-FITC antibody (BD Biosciences) and IC Test IFN γ-PE (Beckman Coulter) using IntraPrep (Beckman Coulter), and a ratio of cells which are CD8-positive and IFN γ-positive was measured with a flow cytometer. FIG. 21 shows an intracellular IFN γ positive cell ratio. The abscissa axis shows the introduced retrovirus, and the ordinate axis shows an IFN γ positive cell rate. As shown in FIG. 21, it was confirmed that by introduction of the T3, T7 or T15 codon modified TCR and siRNA coexpression retroviral vector, the MAGE-A4 antigen-specific IFN γ producing ability is around the same as that of an MS-aPb1-introduced cell as a control.

Example 13

Infection of Human Peripheral Blood Mononuclear Cells with Codon Modified TCR and siRNA Coexpression Retroviral Vector 3

A peripheral blood mononuclear cell (PBMC) separated from human peripheral blood was infected two times with the TN1, TN5 or TN9 codon modified TCR and siRNA coexpression retroviral vector made in Example 7 and, as a control, a codon modified TCR expression pMS-aPb1 vector according to a standard method using RetroNectin, to prepare a codon modified TCR and siRNA coexpression-introduced peripheral blood mononuclear cell. Five days and eleven days after from second virus infection, cells were recovered, real time PCR was carried out according to the same method as that of Example 8, and relative values of expression levels of wild-type TCR α, modified TCR α, wild-type TCR β, and modified TCR β genes were calculated.

Figure 22:
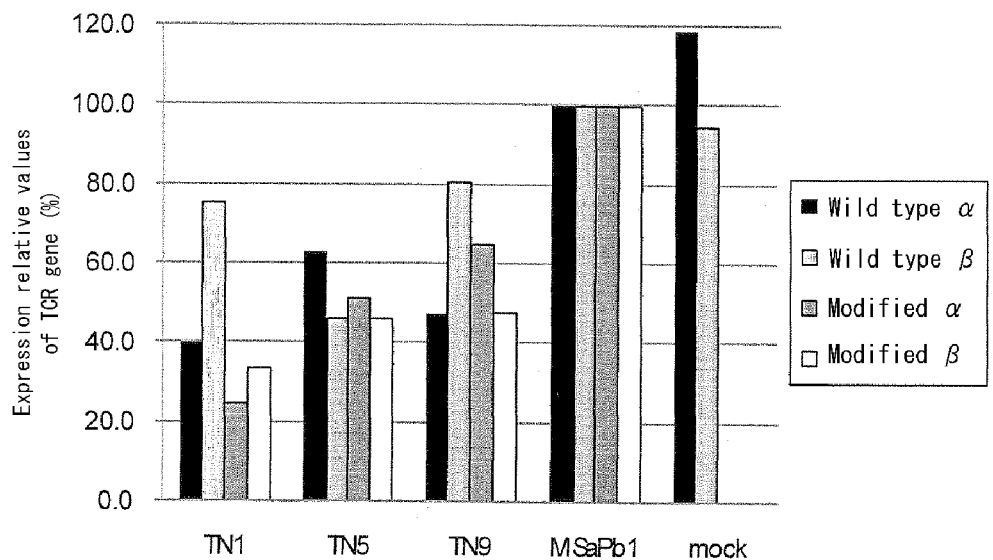
FIG. 22 is a view showing expression of a TCR gene (5 days after infection).
Figure 23:
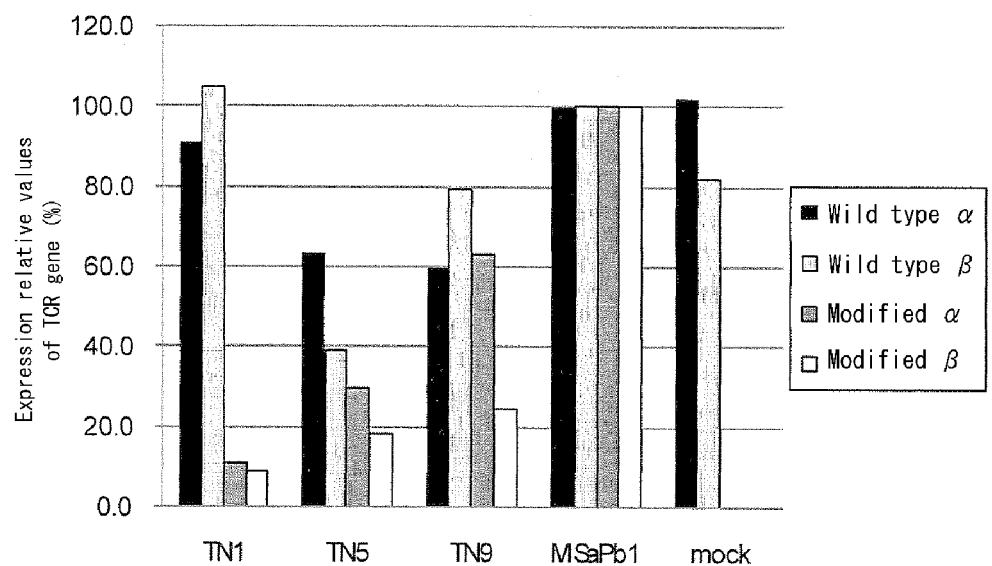
FIG. 23 is a view showing expression of a TCR gene (11 days after infection).

By calculating ratios of expression relative values in each experimental group relative to expression relative values of wild-type TCR α, modified TCR α, wild-type TCR β, and modified TCR β genes in a control experimental group, the wild-type TCR gene silencing effect and an expression level of the modified TCR gene were evaluated. FIG. 22 shows the results after 5 days from infection, and FIG. 23 shows the results after 11 days from infection. In the drawings, the ordinate axis shows expression amounts of wild-type TCR α, modified TCR α, wild-type TCR β, and modified TCR β genes as relative values, assuming values of an MS-aPb1-introduced cell as 100. The abscissa axis shows the introduced retrovirus. As shown in FIG. 22 and FIG. 23, by expression of an siRNA for wild-type TCR α and β, the expressions of the wild-type TCR α and β genes are inhibited in PBMC.

Example 14

Effect of Introduction of Codon Modified TCR and siRNA Coexpression Retroviral Vector on Expression of Codon Modified TCR Protein 3

Figure 24:
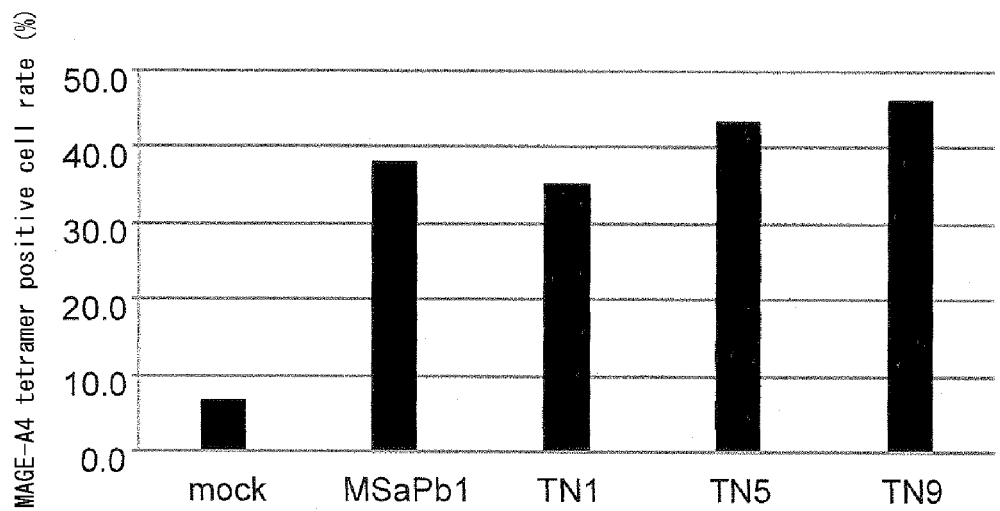
FIG. 24 is a view showing a MAGE-A4 tetramer positive cell rate.

In Example 13, after 4 days from second infection with the TN1, TN5 or TN9 codon modified TCR and siRNA coexpression retrovirus, cells were recovered, and a ratio of cells which are CD8-positive and tetramer-positive was measured according to the same method as that of Example 6. FIG. 24 shows a MAGE-A4 tetramer positive cell ratio after 4 days from virus infection. The abscissa axis shows the introduced retrovirus, and the ordinate axis shows a MAGE-A4 tetramer positive cell ratio. As shown in FIG. 24, by introduction of the TN5 or TN9 codon modified TCR and siRNA coexpression retroviral vector, an expression rate of the modified anti-MAGE-A4 TCR α/β complex protein whose gene had been introduced into a human peripheral blood mononuclear cell was improved as compared with codon modified TCR expression MS-aPb1 as a control. As shown in Example 13, by insertion of the siRNA expression unit, although expression of the modified TCR β gene was lower as compared with the MS-aPb1-introduced cell as a control, enhancement of an expression rate of the modified anti-MAGE-A4 TCR α/β complex protein due to the effect of inhibiting expression of the wild-type TCR gene by an siRNA was observed.

Example 15

Antigen-specific Cytokine Producing Ability of Codon Modified TCR Complex Due to Introduction of Codon Modified TCR and siRNA Coexpression Retroviral Vector 2

Figure 25:
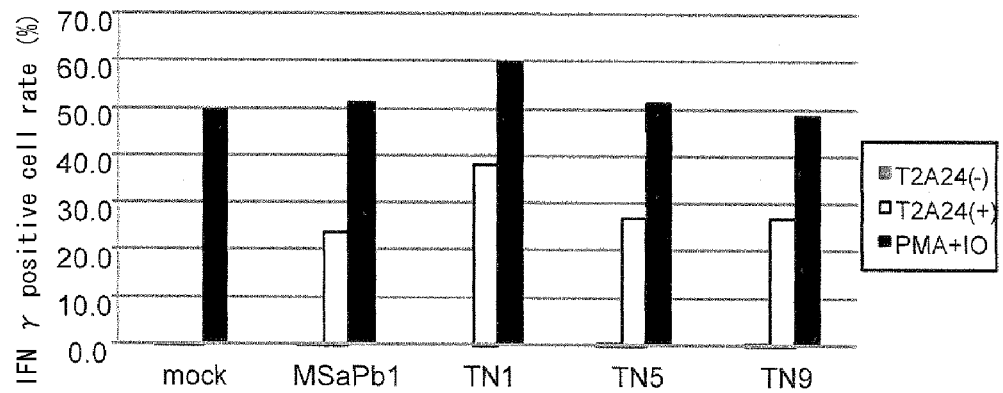
FIG. 25 is a view showing an intracellular IFN γ positive cell rate.

A ratio of cells which are CD8-positive and IFN γ-positive was measured using cells after 4 days from introduction of TN1, TN5, TN9, or MS-aPb1 in Example 13 according to the same method as that of Example 12. FIG. 25 shows an intracellular IFN γ positive cell rate. The abscissa axis shows the introduced retrovirus, and the ordinate axis shows an IFN γ positive cell ratio. As shown in FIG. 25, it was confirmed that by introduction of the TN1, TN5 or TN9 codon modified TCR and siRNA coexpression retroviral vector, the MAGE-A4 antigen-specific IFN γ producing ability is around the same as compared with the MS-aPb1-introduced cell.

Example 16

Infection of Human Peripheral Blood Mononuclear Cells with Codon Modified TCR and siRNA Coexpression Retroviral Vector 4

A peripheral blood mononuclear cell (PBMC) separated from human peripheral blood was infected two times with the TN5 or TN9 codon modified TCR and siRNA coexpression retrovirus prepared in Example 7 as well as a codon modified TCR expression pMS-aPb1 vector as a control according to a standard method using RetroNectin to prepare a codon modified TCR and siRNA coexpression-introduced peripheral blood mononuclear cell.

Figure 26:
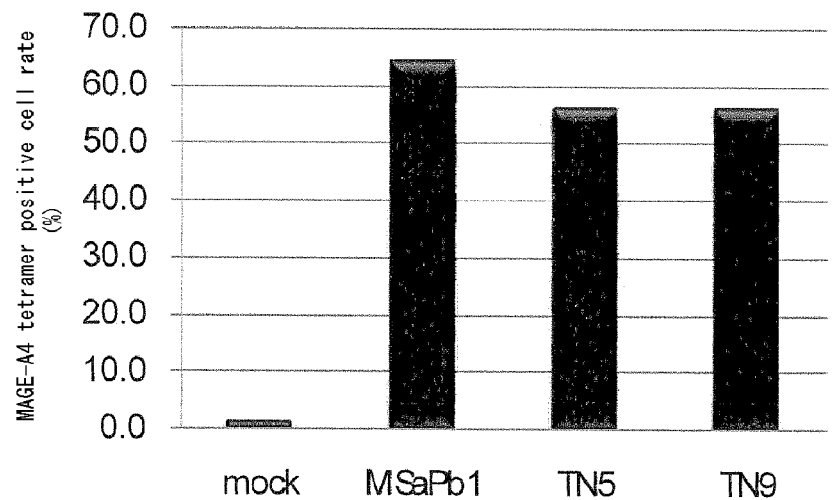
FIG. 26 is a view showing a MAGE-A4 tetramer positive cell rate.

Four days after from second infection, cells were recovered. Average copy numbers of vectors per cell of the TN5, TN9 and MS-aPb1-introduced cells were 3.64, 2.21, and 9.15 copies/cell, respectively. In addition, ratios of cells which are CD8-positive and tetramer-positive were measured according to the same method as that of Example 6. FIG. 26 shows a MAGE-A4 tetramer positive cell ratio after 4 days from virus infection. The abscissa axis shows the introduced retrovirus, and the ordinate axis shows a MAGE-A4 tetramer positive cell ratio. As shown in FIG. 26, by introduction of the TN5 or TN9 codon modified TCR and siRNA coexpression retroviral vector, although the copy number of vectors per cell was smaller than that of MS-aPb1, an expression rate of the modified anti-MAGE-A4 TCR α/β complex protein whose gene had been introduced into a human peripheral blood mononuclear cell was equivalent to that of the codon modified TCR expression MS-aPb1 as a control.

Example 17

Infection of a Human Peripheral Blood Mononuclear Cells with a Codon Modified TCR and siRNA Coexpression Retroviral Vector 4

In Example 16, using a peripheral blood mononuclear cell (PBMC) separated from human peripheral blood, a codon modified TCR and siRNA coexpression-introduced peripheral blood mononuclear cell was prepared. Five days after from virus infection, staining was carried out with a MAGE-A4 tetramer, and only a MAGE-A4 tetramer positive cell was collected with Anti-PE MicroBeads (Miltenyi Biotec). Total RNA extraction from the collected cells and DNaseI treatment were carried out. Real time PCR was carried out according to the same method as that of Example 8, and relative values of expression levels of wild-type TCR α, modified TCR α, wild-type TCR β, and modified TCR β genes were calculated.

Figure 27:
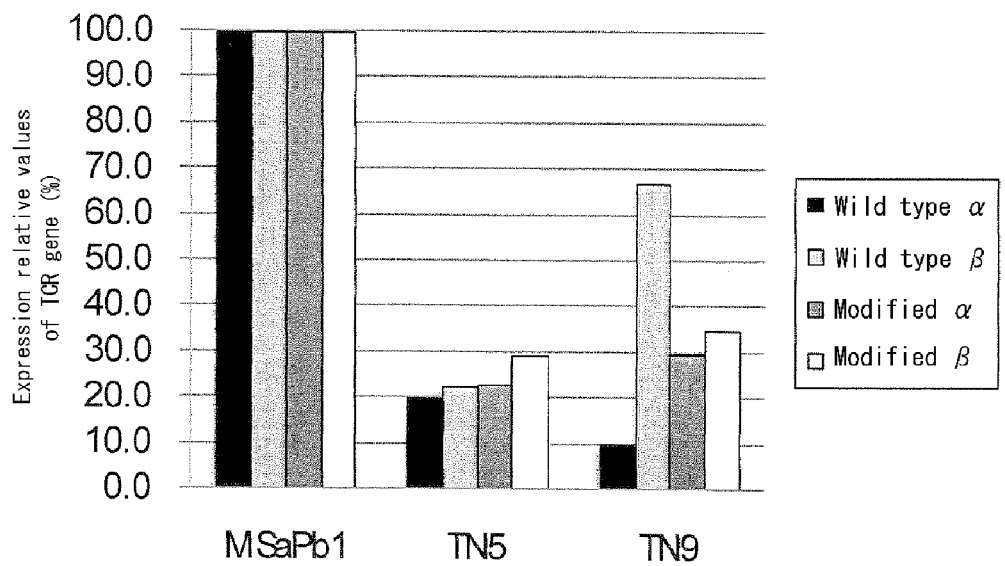
FIG. 27 is a view showing expression of a TCR gene.

By calculating ratios of expression relative values in each experimental group relative to expression relative values of wild-type TCR α, modified TCR α, wild-type TCR β, and modified TCR β genes in a control experimental group, the wild-type TCR gene inhibiting effects and expression levels of the modified TCR gene were evaluated. The results are shown in FIG. 27. In the drawing, the ordinate axis shows expression amounts of wild-type TCR α, modified TCR α, wild-type TCR β, and modified TCR β genes as relative values, assuming values of an MS-aPb1-introduced cell as 100. The abscissa axis shows the introduced retrovirus. As shown in FIG. 27, by expression of an siRNA for wild-type TCR α and β, expressions of the wild-type TCR α and β genes are inhibited in PBMC. In addition, in TN5 and TN9 as compared with pMS-aPb1, although expressions of the modified TCR α and β genes is low, due to inhibition of the endogenous TCR gene by expression of an siRNA for wild-type TCR α and β, as shown in FIG. 26, by introduction of the TN5 or TN9 codon modified TCR and siRNA coexpression retrovirus vector, an expression rate of the modified anti-MAGE-A4 TCR α/β complex protein whose gene had been introduced into a human peripheral blood monocyte was increased to a level equivalent to that of codon modified TCR expression MS-aPb1 as a control.

Industrial Applicability

According to the present invention, there are provided a cell, particularly a T cell, expressing an oligomeric protein useful in the medical field as well as a process for producing the T cell.

Sequence Listing Free Text

SEQ ID NO:1: Codon modified anti-MAGE A4 TCR alpha chain.
SEQ ID NO:2: Codon modified anti-MAGE A4 TCR beta chain.
SEQ ID NO:3: Synthetic chimera oligonucleotide for siRNA-A. Nucleotides 1 to 19 are ribonucleotides-other nucleotides are deoxyribonucleotides
SEQ ID NO:4: Synthetic chimera oligonucleotide for siRNA-A. Nucleotides 1 to 19 are ribonucleotides-other nucleotides are deoxyribonucleotides
SEQ ID NO:5: Synthetic chimera oligonucleotide for siRNA-B. Nucleotides 1 to 19 are ribonucleotides-other nucleotides are deoxyribonucleotides
SEQ ID NO:6: Synthetic chimera oligonucleotide for siRNA-B. Nucleotides 1 to 19 are ribonucleotides-other nucleotides are deoxyribonucleotides
SEQ ID NO:7: Synthetic chimera oligonucleotide for siRNA-C. Nucleotides 1 to 19 are ribonucleotides-other nucleotides are deoxyribonucleotides
SEQ ID NO:8: Synthetic chimera oligonucleotide for siRNA-C. Nucleotides 1 to 19 are ribonucleotides-other nucleotides are deoxyribonucleotides
SEQ ID NO:9: Synthetic oligonucleotide primer for wild-type TCR alpha chain.
SEQ ID NO:10: Synthetic oligonucleotide primer for wild-type TCR alpha chain.
SEQ ID NO:11: Synthetic oligonucleotide primer for codon-modified TCR alpha chain.
SEQ ID NO:12: Synthetic oligonucleotide primer for codon-modified TCR alpha chain.
SEQ ID NO:13: Synthetic oligonucleotide primer for wild-type TCR beta chain.
SEQ ID NO:14: Synthetic oligonucleotide primer for wild-type TCR beta chain.
SEQ ID NO:15: Synthetic oligonucleotide primer for codon-modified TCR beta chain.
SEQ ID NO:16: Synthetic oligonucleotide primer for codon-modified TCR beta chain.
SEQ ID NO:17: Synthetic oligonucleotide primer for beta-actin.
SEQ ID NO:18: Synthetic oligonucleotide primer for beta-actin.
SEQ ID NO:19: Portion of TCR alpha chain.
SEQ ID NO:20: Portion of codon-modified TCR alpha chain.
SEQ ID NO:21: Portion of TCR alpha chain.
SEQ ID NO:22: Portion of TCR beta chain.
SEQ ID NO:23: Portion of codon-modified TCR beta chain.
SEQ ID NO:24: Portion of TCR beta chain.
SEQ ID NO:25: Synthetic oligonucleotide primer pPGK5.
SEQ ID NO:26: Synthetic oligonucleotide primer pPGK3.
SEQ ID NO:27: Synthetic oligonucleotide primer 3MSCV5.
SEQ ID NO:28: Synthetic oligonucleotide primer 3MSCV3.
SEQ ID NO:29: Synthetic oligonucleotide for pSINsi-hU6-TCRA.
SEQ ID NO:30: Synthetic oligonucleotide for pSINsi-hU6-TCRA.
SEQ ID NO:31: Synthetic oligonucleotide for pBAsi-mU6-TCRB.
SEQ ID NO:32: Synthetic oligonucleotide for pBAsi-mU6-TCRB.
SEQ ID NO:33: Synthetic oligonucleotide for TCR-loop-MluI/SacII.
SEQ ID NO:34: Oligonucleotide primer for amplification of GAPDH gene.
SEQ ID NO:35: Oligonucleotide primer for amplification of GAPDH gene.

The invention claimed is:
1. A vector for expressing a non-natural T cell receptor (TCR), comprising:
   (i) recombinant nucleic acid sequences which encode exogenous α and β polypeptide chains that constitute the non-natural TCR and that correspond to endogenous α and β polypeptide chains that constitute a natural TCR having a variable region and a constant region in a target cell in which the vector is to be introduced; and
   (ii) sequences encoding two siRNAs, one which inhibits the expression of the endogenous α polypeptide chain of the natural TCR and the other which inhibits the expression of the endogenous β polypeptide chain of the natural TCR by RNA interference,
wherein:
the siRNAs target a sequence on mRNAs that encode the constant region of each of the endogenous α and β polypeptide chains of the natural TCR, and
each of the nucleotide sequences encoding the exogenous α and β polypeptide chains is modified without changing the encoded amino acid sequence in a region of the polypeptide chain on which one of the siRNAs acts so that the region of the polypeptide chain encodes the same amino acid sequence in the exogenous polypeptide chain as in the corresponding endogenous polypeptide chain, so that the expression of the exogenous α and β polypeptide chains is not inhibited by the siRNAs in the target cell in which the vector is to be introdused.

2. A vector set for expressing a non-natural T cell receptor (TCR), comprising:
   (i) a vector comprising recombinant nucleic acid sequences which encode exogenous α and β polypeptide chains that constitute the non-natural TCR and that correspond to endogenous α and β polypeptide chains that constitute a natural TCR having a variable region and a constant region in a target cell in which the vector is to be introduced; and
   (ii) a vector comprising sequences encoding two siRNAs, one which inhibits the expression of the endogenous α polypeptide chain of the natural TCR and the other which inhibits the expression of the endogenous β polypeptide chain of the natural TCR by RNA interference,
wherein:
the siRNAs target a sequence on mRNAs that encode the constant region of each of the endogenous α and β polypeptide chains of the natural TCR, and
each of the nucleotide sequences encoding the exogenous α and β polypeptide chains is modified without changing the encoded amino acid sequence in a region of the polypeptide chain on which one of the siRNAs acts so that the region of the polypeptide chain encodes the same amino acid sequence in the exogenous polypeptide chain as in the corresponding endogenous polypeptide chain, so that the expression of the exogenous α and β polypeptide chains is not inhibited by the siRNAs in the target cell in which the vector is to be introduced.

* * * * *